United States Patent
Xu et al.

(10) Patent No.: US 12,378,317 B2
(45) Date of Patent: Aug. 5, 2025

(54) PD-L1-BINDING POLYPEPTIDE AND USE THEREOF

(71) Applicant: Suzhou Smartnuclide Biopharmaceutical Co., Ltd., Suzhou (CN)

(72) Inventors: Tao Xu, Suzhou (CN); Yan Sun, Suzhou (CN); Hao Qi, Suzhou (CN); Haijing Du, Suzhou (CN); Tingting Hu, Suzhou (CN); Yanling Yang, Suzhou (CN); Fangfang Li, Suzhou (CN); Qi Zhao, Suzhou (CN); Songbing Qin, Suzhou (CN)

(73) Assignee: Suzhou Smartnuclide Biopharmaceutical Co., Ltd., Jiangsu (CN)

( * ) Notice: Subject to any disclaimer, the term of this patent is extended or adjusted under 35 U.S.C. 154(b) by 833 days.

(21) Appl. No.: 17/137,188

(22) Filed: Dec. 29, 2020

(65) Prior Publication Data

US 2021/0253709 A1     Aug. 19, 2021

Related U.S. Application Data

(63) Continuation of application No. PCT/CN2019/093225, filed on Jun. 27, 2019.

(30) Foreign Application Priority Data

Jun. 29, 2018  (CN) .................... 201810696663.X

(51) Int. Cl.
*C07K 16/28*    (2006.01)
*A61K 51/10*    (2006.01)
*G01N 33/574*   (2006.01)

(52) U.S. Cl.
CPC ...... *C07K 16/2827* (2013.01); *A61K 51/1027* (2013.01); *A61K 51/1045* (2013.01); *G01N 33/57492* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| 10,556,954 B2 * | 2/2020 | Ting | A61P 35/00 |
| 11,466,085 B2 * | 10/2022 | Ting | C12N 15/85 |
| 2019/0177416 A1 * | 6/2019 | Ting | C12N 15/63 |

FOREIGN PATENT DOCUMENTS

| CN | 106397592 A | 2/2017 |
| CN | 107216389 A | 9/2017 |

(Continued)

OTHER PUBLICATIONS

PCT/CN2019/093225, Sep. 11, 2019, International Search Report and Written Opinion and English translations thereof.

(Continued)

*Primary Examiner* — Randall L Beane
(74) *Attorney, Agent, or Firm* — Wolf, Greenfield & Sacks, P.C.

(57) ABSTRACT

The invention relates to the field of biomedicine. Specifically, the invention relates to PD-L1 binding polypeptides and uses thereof in particular, uses m detecting and/or diagnosing PD-L1 related diseases such as cancers.

14 Claims, 14 Drawing Sheets
Specification includes a Sequence Listing.

(56) References Cited

FOREIGN PATENT DOCUMENTS

CN          107686520 A      2/2018
WO      WO-2017157334 A1 *  9/2017  ........... A61K 39/395

OTHER PUBLICATIONS

PCT/CN2019/093225, Jan. 7, 2021, International Preliminary Report on Patentability and English translation thereof.
International Search Report and Written Opinion for Application No. PCT/CN2019/093225, mailed Sep. 11, 2019.
International Preliminary Report on Patentability for Application No. PCT/CN2019/093225, mailed Jan. 7, 2021.

* cited by examiner

Figure 1A
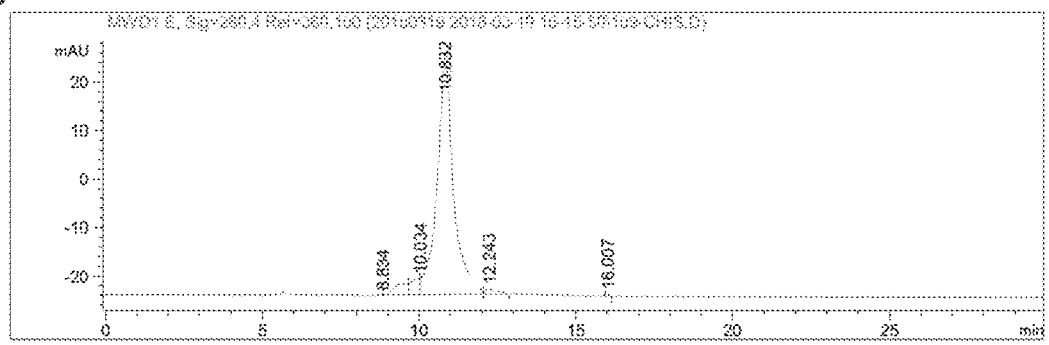
Figure 1B
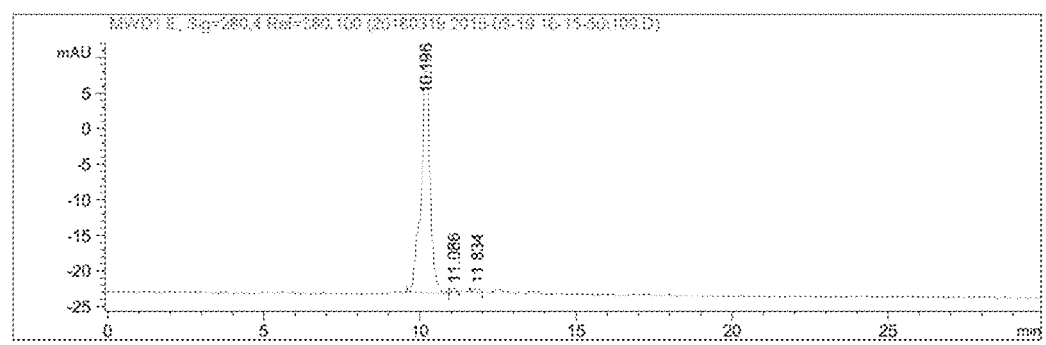
Figure 1C
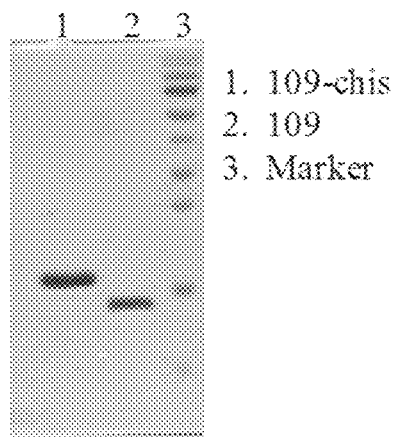
1. 109-chis
2. 109
3. Marker
Figure 1

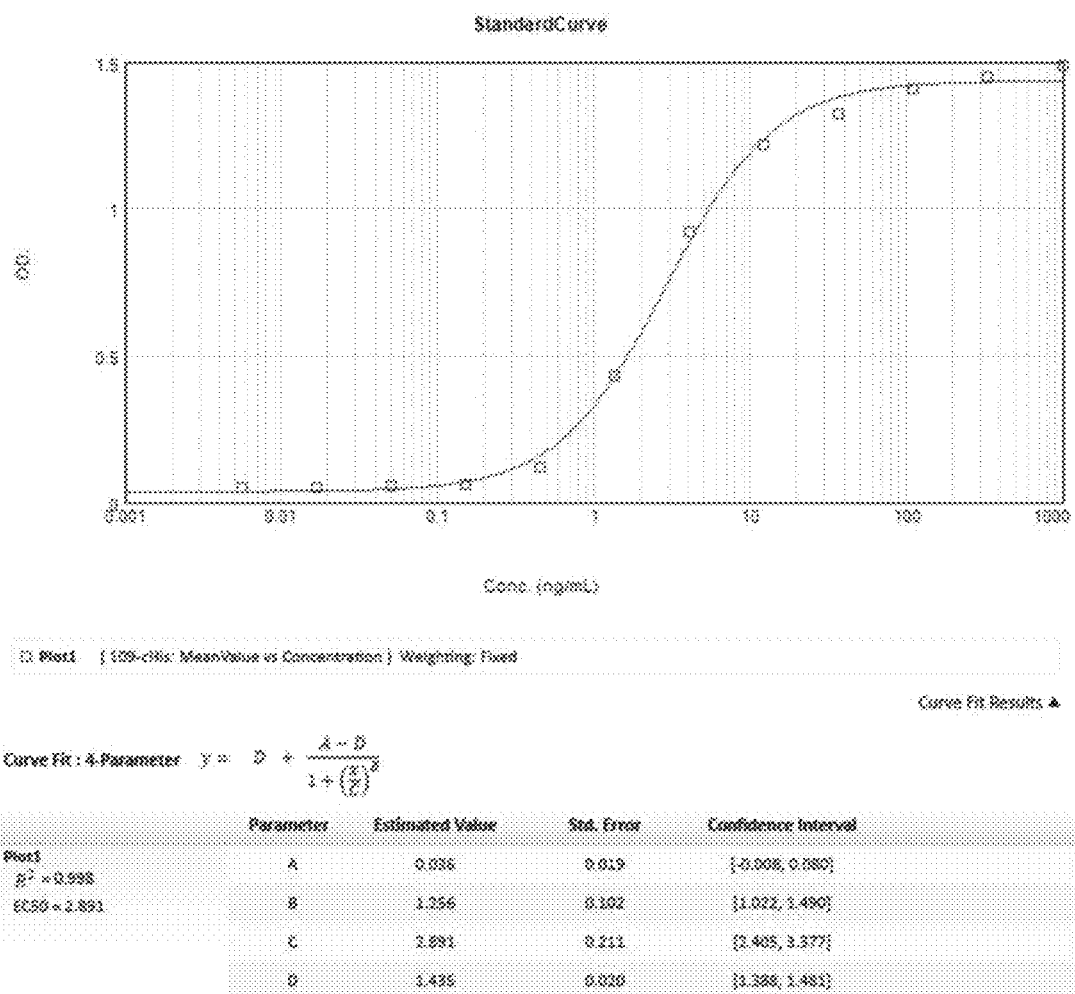
Figure 2  Binding curve of single domain antibody

Figure 6A
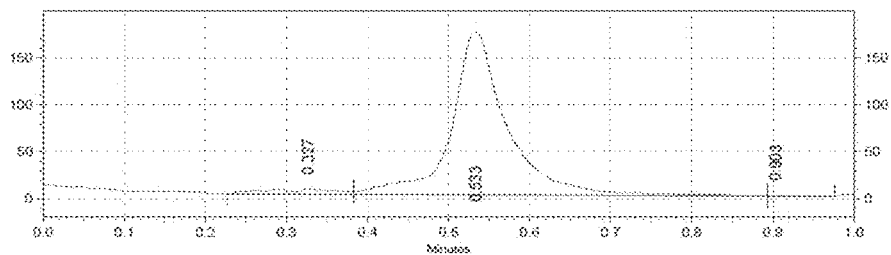
Figure 6B
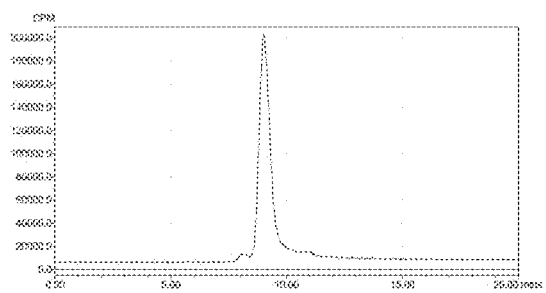
1h
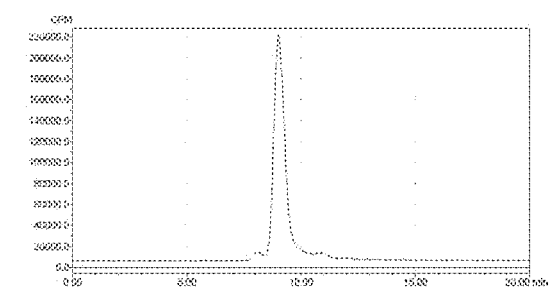
2h
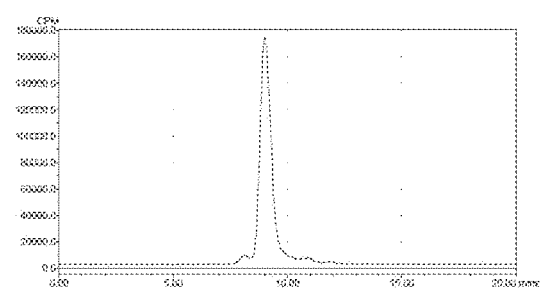
3h
Figure 6C
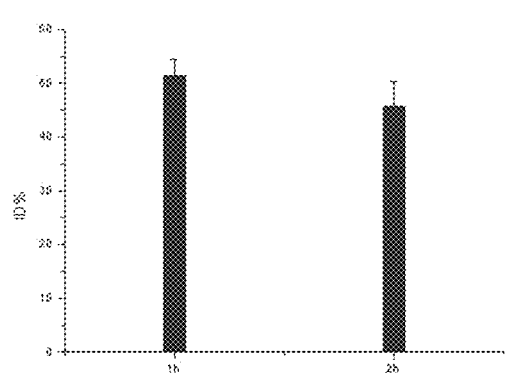

SEQUENCE LISTING

<160> NUMBER OF SEQ ID NOS: 22

<210> SEQ ID NO 1
<211> LENGTH: 126
<212> TYPE: PRT
<213> ORGANISM: Artificial Sequence
<220> FEATURE:
<223> OTHER INFORMATION: 109

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
        35                  40                  45

Ser Thr Ile Ala Ser Asp Arg Ser Thr Tyr Tyr Thr Pro Ser Val Lys
    50                  55                  60

Gly Arg Phe Thr Ile Ser His Asp Arg Ala Lys Asn Thr Ile Tyr Leu
65                  70                  75                  80

Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
        115                 120                 125

<210> SEQ ID NO 2
<211> LENGTH: 142
<212> TYPE: PRT
<213> ORGANISM: Artificial Sequence
<220> FEATURE:
<223> OTHER INFORMATION: 109-chis

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
        35                  40                  45

Ser Thr Ile Ala Ser Asp Arg Ser Thr Tyr Tyr Thr Pro Ser Val Lys
    50                  55                  60

Gly Arg Phe Thr Ile Ser His Asp Arg Ala Lys Asn Thr Ile Tyr Leu
65                  70                  75                  80

Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser Gly Ser
        115                 120                 125

Met Asp Pro Gly Gly Ser His His His His His His
    130                 135                 140

<210> SEQ ID NO 3
<211> LENGTH: 381
<212> TYPE: DNA
<213> ORGANISM: Artificial Sequence
<220> FEATURE:
<223> OTHER INFORMATION: nucleotide sequence of 109 single domain antibody

<400> SEQUENCE: 3
caggtgcagc tgcaggagtc tggaggaggc tcggtgcagg ctggggggtc tctgagactc      60
tcctgtacag cctctggatt cagtttagat gattctgaca tgggctggta ccgccaggct     120

```
cgtgggaatg tgtgccagtt ggtgtcaaca attgctagtg atagaagtac atactataca    180
ccctccgtga agggccgatt caccatctcc catgacagag ccaagaacac aatttatctg    240
caaatgaaca gcctgaaacc tgaggacacg gccgtgtatt actgtgcggc agcccctcgc    300
ctggcctaca acggcgat gacgtgcgag ggggactttg cttactgggg ccagggaacc      360
caggtcaccg tctcctcata a                                              381
```

<210> SEQ ID NO 4
<211> LENGTH: 429
<212> TYPE: DNA
<213> ORGANISM: Artificial Sequence
<220> FEATURE:
<223> OTHER INFORMATION: nucleotide sequence of 109-chis

<400> SEQUENCE: 4

```
caggtgcagc tgcaggagtc tgggggaggc tcggtgcagg ctggggggtc tctgagactc     60
tcctgtacag cctctggatt cagtttagat gattctgaca tgggctggta ccgccaggct   120
cgtgggaatg tgtgccagtt ggtgtcaaca attgctagtg atagaagtac atactataca   180
ccctccgtga agggccgatt caccatctcc catgacagag ccaagaacac aatttatctg   240
caaatgaaca gcctgaaacc tgaggacacg gccgtgtatt actgtgcggc agcccctcgc   300
ctggcctaca acggcgat gacgtgcgag ggggactttg cttactgggg ccagggaacc     360
caggtcaccg tctcctcagg cagcatggat cctggaggat ctcatcatca ccaccaccat   420
catcactaa                                                           429
```

<210> SEQ ID NO 5
<211> LENGTH: 10
<212> TYPE: PRT
<213> ORGANISM: Artificial Sequence
<220> FEATURE:
<223> OTHER INFORMATION: CDR1

<400> SEQUENCE: 5

Gly Phe Ser Leu Asp Asp Ser Asp Met Gly
1               5                   10

<210> SEQ ID NO 6
<211> LENGTH: 15
<212> TYPE: PRT
<213> ORGANISM: Artificial Sequence
<220> FEATURE:
<223> OTHER INFORMATION: CDR2

<400> SEQUENCE: 6

Ile Ala Ser Asp Arg Ser Thr Tyr Tyr Thr Pro Ser Val Lys Gly
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: CDR3

<400> SEQUENCE: 7

Ala Pro Arg Leu Ala Tyr Thr Thr Ala Met Thr Cys Glu Gly Asp Phe
1               5                   10                  15

Ala Tyr

<210> SEQ ID NO 8

```
<211> LENGTH: 162
<212> TYPE: PRT
<213> ORGANISM: Artificial Sequence
<220> FEATURE:
<223> OTHER INFORMATION: 109-K86R&P87A-cHis

<400> SEQUENCE: 8

Met Glu Thr Asp Thr Leu Leu Leu Trp Val Leu Leu Trp Val Pro
1               5                   10                  15

Gly Ser Thr Gly Gln Val Gln Leu Gln Glu Ser Gly Gly Gly Ser Val
            20                  25                  30

Gln Ala Gly Gly Ser Leu Arg Leu Ser Cys Thr Ala Ser Gly Phe Ser
        35                  40                  45

Leu Asp Asp Ser Asp Met Gly Trp Tyr Arg Gln Ala Arg Gly Asn Val
    50                  55                  60

Cys Gln Leu Val Ser Thr Ile Ala Ser Asp Arg Ser Thr Tyr Tyr Thr
65                  70                  75                  80

Pro Ser Val Lys Gly Arg Phe Thr Ile Ser His Asp Arg Ala Lys Asn
                85                  90                  95

Thr Ile Tyr Leu Gln Met Asn Ser Leu Arg Ala Glu Asp Thr Ala Val
            100                 105                 110

Tyr Tyr Cys Ala Ala Ala Pro Arg Leu Ala Tyr Thr Thr Ala Met Thr
        115                 120                 125

Cys Glu Gly Asp Phe Ala Tyr Trp Gly Gln Gly Thr Gln Val Thr Val
    130                 135                 140

Ser Ser Gly Ser Met Asp Pro Gly Gly Ser His His His His His His
145                 150                 155                 160

His His

<210> SEQ ID NO 9
<211> LENGTH: 162
<212> TYPE: PRT
<213> ORGANISM: Artificial Sequence
<220> FEATURE:
<223> OTHER INFORMATION: 109-RDNSE-cHis

<400> SEQUENCE: 9

Met Glu Thr Asp Thr Leu Leu Leu Trp Val Leu Leu Trp Val Pro
1               5                   10                  15

Gly Ser Thr Gly Gln Val Gln Leu Gln Glu Ser Gly Gly Gly Ser Val
            20                  25                  30

Gln Ala Gly Gly Ser Leu Arg Leu Ser Cys Thr Ala Ser Gly Phe Ser
        35                  40                  45

Leu Asp Asp Ser Asp Met Gly Trp Tyr Arg Gln Ala Arg Gly Asn Val
    50                  55                  60

Cys Gln Leu Val Ser Thr Ile Ala Ser Asp Arg Ser Thr Tyr Tyr Thr
65                  70                  75                  80

Pro Ser Val Lys Gly Arg Phe Thr Ile Ser Arg Asp Asn Ser Glu Asn
                85                  90                  95

Thr Ile Tyr Leu Gln Met Asn Ser Leu Lys Pro Glu Asp Thr Ala Val
            100                 105                 110

Tyr Tyr Cys Ala Ala Ala Pro Arg Leu Ala Tyr Thr Thr Ala Met Thr
        115                 120                 125

Cys Glu Gly Asp Phe Ala Tyr Trp Gly Gln Gly Thr Gln Val Thr Val
    130                 135                 140

Ser Ser Gly Ser Met Asp Pro Gly Gly Ser His His His His His His
145                 150                 155                 160
```

His His

<210> SEQ ID NO 10
<211> LENGTH: 162
<212> TYPE: PRT
<213> ORGANISM: Artificial Sequence
<220> FEATURE:
<223> OTHER INFORMATION: 109-K64Q-cHis

<400> SEQUENCE: 10

```
Met Glu Thr Asp Thr Leu Leu Leu Trp Val Leu Leu Leu Trp Val Pro
1               5                   10                  15
Gly Ser Thr Gly Gln Val Gln Leu Gln Glu Ser Gly Gly Gly Ser Val
            20                  25                  30
Gln Ala Gly Gly Ser Leu Arg Leu Ser Cys Thr Ala Ser Gly Phe Ser
        35                  40                  45
Leu Asp Asp Ser Asp Met Gly Trp Tyr Arg Gln Ala Arg Gly Asn Val
    50                  55                  60
Cys Gln Leu Val Ser Thr Ile Ala Ser Asp Arg Ser Thr Tyr Tyr Thr
65                  70                  75                  80
Pro Ser Val Gln Gly Arg Phe Thr Ile Ser His Asp Arg Ala Lys Asn
                85                  90                  95
Thr Ile Tyr Leu Gln Met Asn Ser Leu Lys Pro Glu Asp Thr Ala Val
            100                 105                 110
Tyr Tyr Cys Ala Ala Ala Pro Arg Leu Ala Tyr Thr Thr Ala Met Thr
        115                 120                 125
Cys Glu Gly Asp Phe Ala Tyr Trp Gly Gln Gly Thr Gln Val Thr Val
    130                 135                 140
Ser Ser Gly Ser Met Asp Pro Gly Gly Ser His His His His His His
145                 150                 155                 160
His His
```

<210> SEQ ID NO 11
<211> LENGTH: 162
<212> TYPE: PRT
<213> ORGANISM: Artificial Sequence
<220> FEATURE:
<223> OTHER INFORMATION: 109-R73N&K75E-cHis

<400> SEQUENCE: 11

```
Met Glu Thr Asp Thr Leu Leu Leu Trp Val Leu Leu Leu Trp Val Pro
1               5                   10                  15
Gly Ser Thr Gly Gln Val Gln Leu Gln Glu Ser Gly Gly Gly Ser Val
            20                  25                  30
Gln Ala Gly Gly Ser Leu Arg Leu Ser Cys Thr Ala Ser Gly Phe Ser
        35                  40                  45
Leu Asp Asp Ser Asp Met Gly Trp Tyr Arg Gln Ala Arg Gly Asn Val
    50                  55                  60
Cys Gln Leu Val Ser Thr Ile Ala Ser Asp Arg Ser Thr Tyr Tyr Thr
65                  70                  75                  80
Pro Ser Val Lys Gly Arg Phe Thr Ile Ser His Asp Asn Ala Glu Asn
                85                  90                  95
Thr Ile Tyr Leu Gln Met Asn Ser Leu Lys Pro Glu Asp Thr Ala Val
            100                 105                 110
Tyr Tyr Cys Ala Ala Ala Pro Arg Leu Ala Tyr Thr Thr Ala Met Thr
        115                 120                 125
```

```
Cys Glu Gly Asp Phe Ala Tyr Trp Gly Gln Gly Thr Gln Val Thr Val
            130                 135                 140

Ser Ser Gly Ser Met Asp Pro Gly Gly Ser His His His His His His
145                 150                 155                 160

His His
```

<210> SEQ ID NO 12
<211> LENGTH: 162
<212> TYPE: PRT
<213> ORGANISM: Artificial Sequence
<220> FEATURE:
<223> OTHER INFORMATION: 109-K64Q-RDNSE-cHis

<400> SEQUENCE: 12

```
Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Gly Gly Ser Val
                20                  25                  30

Gln Ala Gly Gly Ser Leu Arg Leu Ser Cys Thr Ala Ser Gly Phe Ser
            35                  40                  45

Leu Asp Asp Ser Asp Met Gly Trp Tyr Arg Gln Ala Arg Gly Asn Val
        50                  55                  60

Cys Gln Leu Val Ser Thr Ile Ala Ser Asp Arg Ser Thr Tyr Tyr Thr
65                  70                  75                  80

Pro Ser Val Gln Gly Arg Phe Thr Ile Ser Arg Asp Asn Ser Glu Asn
                85                  90                  95

Thr Ile Tyr Leu Gln Met Asn Ser Leu Lys Pro Glu Asp Thr Ala Val
            100                 105                 110

Tyr Tyr Cys Ala Ala Ala Pro Arg Leu Ala Tyr Thr Thr Ala Met Thr
        115                 120                 125

Cys Glu Gly Asp Phe Ala Tyr Trp Gly Gln Gly Thr Gln Val Thr Val
    130                 135                 140

Ser Ser Gly Ser Met Asp Pro Gly Gly Ser His His His His His His
145                 150                 155                 160

His His
```

<210> SEQ ID NO 13
<211> LENGTH: 15
<212> TYPE: PRT
<213> ORGANISM: Artificial Sequence
<220> FEATURE:
<223> OTHER INFORMATION: mutated CDR2

<400> SEQUENCE: 13

```
Ile Ala Ser Asp Arg Ser Thr Tyr Tyr Thr Pro Ser Val Gln Gly
1               5                   10                  15
```

<210> SEQ ID NO 14
<211> LENGTH: 24
<212> TYPE: DNA
<213> ORGANISM: Artificial Sequence
<220> FEATURE:
<223> OTHER INFORMATION: upstream primer for first round

<400> SEQUENCE: 14
gtcctggctg ctcttctaca aggc                                      24

<210> SEQ ID NO 15
<211> LENGTH: 23
<212> TYPE: DNA

<213> ORGANISM: Artificial Sequence
<220> FEATURE:
<223> OTHER INFORMATION: downstream primer for first round

<400> SEQUENCE: 15
ggtacgtgct gttgaactgt tcc                                          23

<210> SEQ ID NO 16
<211> LENGTH: 29
<212> TYPE: DNA
<213> ORGANISM: Artificial Sequence
<220> FEATURE:
<223> OTHER INFORMATION: upstream primer for second round

<400> SEQUENCE: 16
gatgtgcagc tgcaggagtc tggrggagg                                    29

<210> SEQ ID NO 17
<211> LENGTH: 35
<212> TYPE: DNA
<213> ORGANISM: Artificial Sequence
<220> FEATURE:
<223> OTHER INFORMATION: downstream primer for second round

<400> SEQUENCE: 17
ggactagtgc ggccgctgga gacggtgacc tgggt                             35

<210> SEQ ID NO 18
<211> LENGTH: 126
<212> TYPE: PRT
<213> ORGANISM: Artificial Sequence
<220> FEATURE:
<223> OTHER INFORMATION: 109-K86R&P87A

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
        35                  40                  45

Ser Thr Ile Ala Ser Asp Arg Ser Thr Tyr Tyr Thr Pro Ser Val Lys
    50                  55                  60

Gly Arg Phe Thr Ile Ser His Asp Arg Ala Lys Asn Thr Ile Tyr Leu
65                  70                  75                  80

Gln Met Asn Ser Leu Arg Ala Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
        115                 120                 125

<210> SEQ ID NO 19
<211> LENGTH: 126
<212> TYPE: PRT
<213> ORGANISM: Artificial Sequence
<220> FEATURE:
<223> OTHER INFORMATION: 109-RDNSE

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
            35                  40                  45

Ser Thr Ile Ala Ser Asp Arg Ser Thr Tyr Tyr Thr Pro Ser Val Lys
        50                  55                  60

Gly Arg Phe Thr Ile Ser Arg Asp Asn Ser Glu Asn Thr Ile Tyr Leu
65                  70                  75                  80

Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
            115                 120                 125

<210> SEQ ID NO 20
<211> LENGTH: 126
<212> TYPE: PRT
<213> ORGANISM: Artificial Sequence
<220> FEATURE:
<223> OTHER INFORMATION: 109-K64Q

<400> SEQUENCE: 20

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
            35                  40                  45

Ser Thr Ile Ala Ser Asp Arg Ser Thr Tyr Tyr Thr Pro Ser Val Gln
        50                  55                  60

Gly Arg Phe Thr Ile Ser His Asp Arg Ala Lys Asn Thr Ile Tyr Leu
65                  70                  75                  80

Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
            115                 120                 125

<210> SEQ ID NO 21
<211> LENGTH: 126
<212> TYPE: PRT
<213> ORGANISM: Artificial Sequence
<220> FEATURE:
<223> OTHER INFORMATION: 109-R73N&K75E

<400> SEQUENCE: 21

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
            35                  40                  45

Ser Thr Ile Ala Ser Asp Arg Ser Thr Tyr Tyr Thr Pro Ser Val Lys
        50                  55                  60

Gly Arg Phe Thr Ile Ser His Asp Asn Ala Glu Asn Thr Ile Tyr Leu
65                  70                  75                  80

```
Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
            115                 120                 125

<210> SEQ ID NO 22
<211> LENGTH: 126
<212> TYPE: PRT
<213> ORGANISM: Artificial Sequence
<220> FEATURE:
<223> OTHER INFORMATION: 109-K64Q-RDNSE

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Ser Leu Asp Asp Ser
            20                  25                  30

Asp Met Gly Trp Tyr Arg Gln Ala Arg Gly Asn Val Cys Gln Leu Val
            35                  40                  45

Ser Thr Ile Ala Ser Asp Arg Ser Thr Tyr Tyr Thr Pro Ser Val Gln
        50                  55                  60

Gly Arg Phe Thr Ile Ser Arg Asp Asn Ser Glu Asn Thr Ile Tyr Leu
65                  70                  75                  80

Gln Met Asn Ser Leu Lys Pro Glu Asp Thr Ala Val Tyr Tyr Cys Ala
                85                  90                  95

Ala Ala Pro Arg Leu Ala Tyr Thr Thr Ala Met Thr Cys Glu Gly Asp
            100                 105                 110

Phe Ala Tyr Trp Gly Gln Gly Thr Gln Val Thr Val Ser Ser
            115                 120                 125
```

PD-L1-BINDING POLYPEPTIDE AND USE THEREOF

RELATED APPLICATIONS

This Application is a continuation of International Patent Application Serial No. PCT/CN2019/093225, filed Jun. 27, 2019, which claims priority to Chinese application number 201810696663.X, filed Jun. 29, 2018. The entire contents of each of these applications are incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 29, 2020, is named 5216070000U500-SEQ-JAV.txt, and is 19,286 bytes in size.

TECHNICAL FIELD

The invention relates to the field of biomedicine. Specifically, the invention relates to a specific PD-L1 binding polypeptide and uses thereof, in particular, uses in detecting and/or diagnosing PD-L1 related diseases such as cancers.

BACKGROUND

Programmed death-1 (PD-1) is a member of the CD28 receptor family, which includes CD28, CTLA-4, ICOS, PD-1, and BTLA. The first members of this family, CD28 and ICOS, were discovered through enhancement of T cell proliferation by the addition of monoclonal antibodies (Hutloff et al. (1999), Nature 397: 263-266; Hansen et al. (1980), Immunogenics 10: 247-260). Two cell surface glycoprotein ligands, PD-L1 and PD-L2, have been identified and have been shown to down-regulate T cell activation and cytokine secretion upon binding to PD-1 (Freeman et al. (2000), J Exp Med 192:1027-34; Latchman et al (2001), Nat Immunol 2:261-8; Cater et al (2002), Eur J Immunol 32:634-43; Ohigashi et al (2005), Clin Cancer Res 11:2947-53). Both PD-L1 (B7-H1) and PD-L2 (B7-DC) are B7 homologs that bind to PD-1 but do not bind to other CD28 family members (Blank et al. 2004). Expression of PD-L1 has been found in several murine and human cancers, including human lung cancer, ovarian cancer, colon cancer, melanoma, and various myeloma (Iwai et al. (2002), PNAS 99: 12293-7; Ohigashi et al (2005), Clin Cancer Res 11: 2947-53). Currently available results have shown that PD-L1, which is highly expressed in tumor cells, plays an important role in the immune escape of tumors by increasing apoptosis of T cells. Detecting the expression of PD-L1 in patients can be used for tumor diagnoses, or to provide a clinical diagnosis basis for anti-PD1 or anti-PD-L1 tumor immunotherapies. However, previously reported antibodies against PD-L1 have not been successfully used to effectively detect and/or diagnose cancers at early stages.

Emission Computed Tomography (ECT) has been used for tumor diagnoses. ECT includes Single-Photon Emission Computed Tomography (SPECT) and Positron Emission Tomography (PET), which provide high-resolution tumor imaging and quantitative analysis through images.

There are needs of a diagnostic agent that can be used to detect PD-L1 expressing tumor cells, in particular a PD-L1 antibody-based diagnostic agent suitable for ECT detection.

SUMMARY OF THE INVENTION

The invention combines traditional PET technology with antibodies and similar molecules, and uses antibodies to identify target cells, thereby providing a snapshot of all tumors in the body. The invention relates to tools using PD-L1 heavy chain single domain antibodies (VHH) or derivative molecules as imaging agents to identify interesting cells.

In one aspect, the invention provides a programmed death ligand 1 (PD-L1) binding polypeptide, characterized by being capable of specifically binding to PD-L1 and comprising at least one immunoglobulin single variable domain, wherein the at least one immunoglobulin single variable domain comprises:

CDR1, which comprises an amino acid sequence set forth in SEQ ID NO: 5 or an amino acid sequence having one or more amino acid residue substitutions, deletions or additions compared to SEQ ID NO: 5, CDR2, which comprises an amino acid sequence set forth in SEQ ID NO: 6 or an amino acid sequence having one or more amino acid residue substitutions, deletions or additions compared to SEQ ID NO: 6, for example, comprising an amino acid sequence set forth in SEQ ID NO: 13, and CDR3, which comprises an amino acid sequence set forth in SEQ ID NO: 7 or an amino acid sequence having one or more amino acid residue substitutions, deletions or additions compared to SEQ ID NO: 7.

In some specific embodiments, the at least one immunoglobulin single variable domain comprises:

CDR1, which comprises the amino acid sequence set forth in SEQ ID NO: 5,

CDR2, which comprises the amino acid sequence set forth in SEQ ID NO: 13, and

CDR3, which comprises the amino acid sequence set forth in SEQ ID NO:7.

In some embodiments, the immunoglobulin single variable domain comprises an amino acid sequence that is at least 80%, preferably at least 90%, more preferably at least 95%, even more preferably at least 99% identical to the amino acid sequence of SEQ ID NO:1.

In some embodiments, the immunoglobulin single variable domain comprises only one lysine residue. In some embodiments, the immunoglobulin single variable domain comprises an amino acid sequence selected from the group consisting of SEQ ID NO: 1-2, 8-12, and 18-22.

In some embodiments, the immunoglobulin single variable domain is VHH.

In some embodiments, the PD-L1 binding polypeptide does not block binding of PD-1 to PD-L1.

In another aspect, the invention provides a nucleic acid molecule encoding the PD-L1 binding polypeptide of the invention.

In another aspect, the invention provides an expression vector comprising the nucleic acid molecule of the invention operably linked to an expression regulatory element.

In another aspect, the invention provides a host cell comprising the nucleic acid molecule of the invention or transformed with the expression vector of the invention, and capable of expressing the PD-L1 binding polypeptide.

In another aspect, the invention provides a method for producing the PD-L1 binding polypeptide of the invention, comprising:

a) culturing the host cell of the invention under conditions that enable expression of the PD-L1 binding polypeptide;

b) recovering the PD-L1 binding polypeptide expressed by the host cell from the culture obtained from step a); and c) optionally further purifying and/or modifying the PD-L1 binding polypeptide obtained from step b).

In another aspect, the invention provides a conjugated molecule comprising the PD-L1 binding polypeptide of the invention and at least one detectable marker conjugated to the PD-L1 binding polypeptide.

In some embodiments, the detectable marker is selected from the group consisting of radionuclides, fluorescent agents, chemiluminescent agents, bioluminescent agents, paramagnetic ions, and enzymes.

In some embodiments, the detectable marker is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{68}$Ge, $^{86}$Y, $^{90}$Y, $^{89}$Zr, $^{94m}$Tc, $^{120}$I, $^{123}$I, $^{124}$I, $^{125}$I, $^{131}$I, $^{154-158}$Gd $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr or other γ-, β-, or positron emitters. For example, the detectable marker is $^{68}$Ga or $^{125}$I.

In some embodiments, the PD-L1 binding polypeptide is conjugated to the detectable marker through a chelating agent.

In some embodiments, the chelating agent is selected from the group consisting of NOTA, DOTA, TETA or NETA.

In some embodiments, the detectable marker is $^{68}$Ga and the chelating agent is NOTA.

In some embodiments, the PD-L1 binding polypeptide comprises the amino acid sequence set forth in SEQ ID NO: 12 or 22.

In another aspect, the invention provides a method for detecting the presence of PD-L1 and/or expression level of PD-L1 in a biological sample, comprising:
a) contacting the biological sample and the control sample to the PD-L1 binding polypeptide of the invention and/or the conjugated molecule of the invention under the condition that the PD-L1 binding polypeptide of the invention and/or the conjugated molecule of the invention can form a complex with PD-L1;
b) detecting complex formation,
wherein difference in the complex formation between the biological sample and the control sample is indicative of the presence of PD-L1 and/or the expression level of PD-L1 in the sample.

In another aspect, the invention provides a diagnostic agent for detecting and/or diagnosing PD-L1 related diseases such as cancers, comprising the PD-L1 binding polypeptide of the invention and/or the conjugated molecule of the invention, and optionally a physiologically acceptable carrier. In some embodiments, the diagnostic agent is an ECT contrast agent, such as a SPECT contrast agent or a PET contrast agent.

In another aspect, the invention provides use of the PD-L1 binding polypeptide of the invention and/or the conjugated molecule of the invention in manufacturing a diagnostic agent for detecting and/or diagnosing PD-L1 related diseases such as cancers. In some embodiments, the diagnostic agent is an ECT contrast agent, such as a SPECT contrast agent or a PET contrast agent.

In another aspect, the invention provides a method for detecting and/or diagnosing a PD-L1 related disease such as a cancer in a subject, comprising administering the PD-L1 binding polypeptide of the invention and/or the conjugated molecules of the invention and/or the diagnostic agent of the invention to the subject.

In some embodiments, the method further comprises the step of performing imaging such as ECT imaging to the subject. In some embodiments, the ECT imaging is SPECT imaging. In some embodiments, the ECT imaging is PET imaging.

In some embodiments of various aspects of the invention, the cancer highly expresses PD-L1. For example, the cancer is selected from the group consisting of lung cancer, ovarian cancer, colon cancer, rectal cancer, melanoma, bladder cancer, breast cancer, liver cancer, lymphoma, hematological malignancies, head and neck cancer, glioma, stomach cancer, nasopharyngeal cancer, laryngeal cancer, cervical cancer, corpus carcinoma, osteosarcoma.

In another aspect, the invention provides a kit comprising the PD-L1 binding polypeptide of the invention and/or the conjugated molecule of the invention and/or the diagnostic agent of the invention.

BRIEF DESCRIPTION OF THE DRAWINGS

FIGS. 1A-1C illustrate biochemical analyses of a heavy-chain single domain antibody 109, wherein FIG. 1A and FIG. 1B show SEC-HPLC analyses of 109-chis and 109, respectively, and FIG. 1C shows SDS-PAGE analyses of the purified proteins of 109-chis and 109.

FIG. 2 illustrates a binding curve of 109-chis and PD-L1.

FIG. 3A illustrates a competitive ELISA curve of 109-chis, FIG. 3B illustrates binding effect of 109-chis to PD-L1 on cell surface by a flow-cytometry, and FIG. 3C illustrates an immunohistochemical result of 109-chis in animal tumor sections.

FIGS. 4A-4D illustrate labeling of the single domain antibody with a positron nuclide, wherein FIG. 4A shows a flow chart of conjugating the single domain antibody with a chelating agent and a radionuclide $^{68}$Ga, FIG. 4B shows mass spectrometry analyses of proteins 109 and 109-NOTA, FIG. 4C shows mass spectrum analyses of $^{67}$Ga-NOTA-109, and FIG. 4D shows binding curves and EC50 values of $^{67}$Ga-NOTA-109-chis to PD-L1.

FIGS. 5A-5C illustrate identification and analyses of a mutant 109-K64Q-RDNSE-cHis, wherein FIG. 5A shows ELISA activity analyses of mutants 109-R73N&K75E-cHis and 109-K86R&P87A-cHis, FIG. 5B shows ELISA activity analyses of mutated antibodies 109-RDNSE-cHis and 109-K64Q-cHis, and FIG. 5C shows mass spectrometry analyses of NOTA conjugates of the mutants.

FIGS. 6A-6C illustrate the in vitro analyses of the positron nuclide labeled single domain antibody $^{68}$Ga-NOTA-109, wherein FIG. 6A shows an ITLC analysis of $^{68}$Ga-NOTA-109-chis, FIG. 6B shows SEC-HPLC and in vitro stability of $^{68}$Ga-NOTA-109-chis, and FIG. 6C is a result of an endocytosis test of $^{68}$Ga-NOTA-109-chis.

FIGS. 7A-7D illustrate in vivo distribution of $^{68}$Ga-NOTA-109, wherein FIG. 7A shows in vivo distribution of $^{68}$Ga-NOTA-109-chis in various tissues, FIG. 7B shows tumor to organ ratios of $^{68}$Ga-NOTA-109-chis in vivo distribution, and FIG. 7C shows in vivo PET imaging of $^{68}$Ga-NOTA-109-chis, and FIG. 7D shows in vivo biodistribution curves of $^{68}$Ga-NOTA-109-chis.

DETAILED DESCRIPTION OF THE INVENTION

Definitions

Figure 3A:
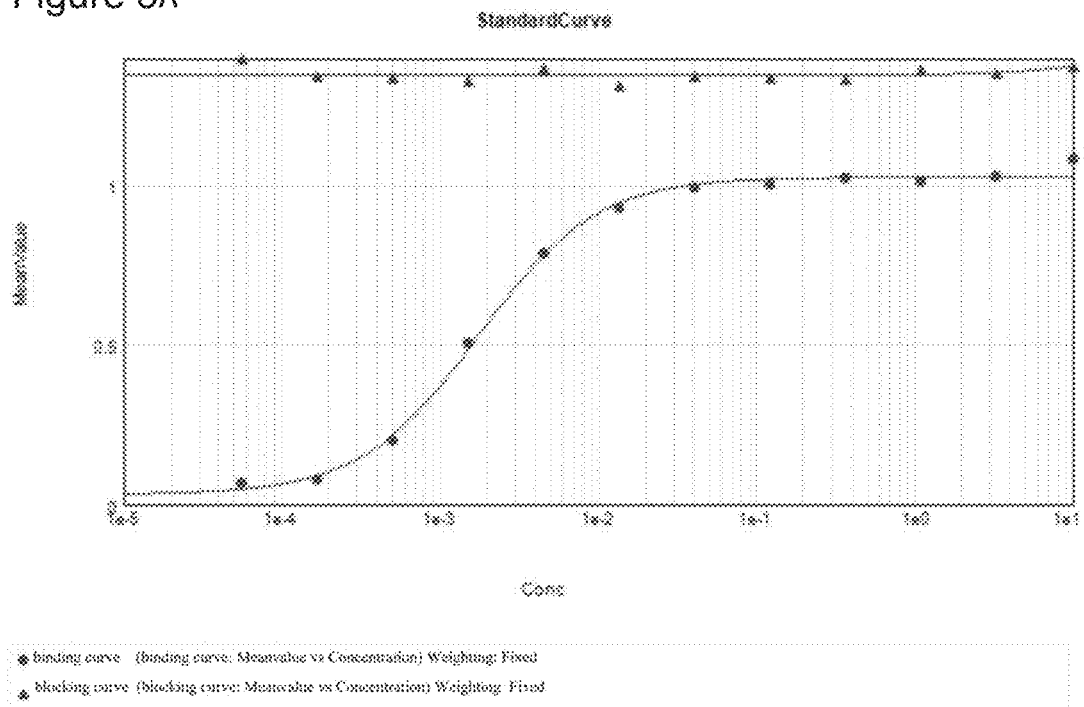
FIGS. 3A-3C illustrate the in vitro activity of the heavy-chain single domain antibody of PD-L1.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); Lewin, "Genes IV", Oxford University Press, New York, (1990); and Roitt et al., "Immunology" (2nd edition), Gower Medical Publishing, London, New York (1989), and the general prior arts cited herein. In addition, unless otherwise stated, all methods, steps, techniques, and operations that are not specifically detailed can be and have been performed in a manner known per se, which will be clear to the skilled person. Reference is also for example made to the standard manual, the above-mentioned general prior arts and other references cited herein.

Unless indicated otherwise, the term "antibody" or "immunoglobulin" used interchangeably herein", whether refer to a heavy chain antibody or to a conventional 4-chain antibody, are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or"FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the invention is "domain antibodies", such as the immunoglobulin single variable domains VH and VL (VH domains and VL domains). Another example of immunoglobulin single variable domains is "VHH domains" (or simply "VHHs") from camelids, as defined hereinafter. "VHH domains", also known as VHHs, $V_HH$ domains, VHH antibody fragments, and VHH antibodies, have originally been described as the antigen binding immunoglobulin (variable) domain of "heavy chain antibodies" (i.e. "antibodies devoid of light chains") (Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the invention, the terms "Heavy chain single domain antibody", "VHH domain", "VHH", "$V_HH$ domain", "VHH antibody fragment", and "VHH antibody", as well as "Nanobody®" and "Nanobody® domain" ("Nanobody" being a trademark of the company Ablynx N.V.; Ghent; Belgium) are used interchangeably.

The amino acid residues of a immunoglobulin single variable domain, e.g. a VHH, are numbered according to the general numbering for VH domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering, FR1 comprises the amino acid residues at positions 1-30, CDR1 comprises the amino acid residues at positions 31-35, FR2 comprises the amino acids at positions 36-49, CDR2 comprises the amino acid residues at positions 50-65, FR3 comprises the amino acid residues at positions 66-94, CDR3 comprises the amino acid residues at positions 95-102, and FR4 comprises the amino acid residues at positions 103-113.

However, it should be noted that, as is well known in the art for VH domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may comprise more amino acid residues than the number enabled for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present description, claims and figures, the numbering according to Kabat and applied to VHH domains as described above will be followed, unless indicated otherwise. The total number of amino acid residues in a VHH domain will usually be in the range of from 110 to 120, often between 112 and 115. It should however be noted that smaller and longer sequences may also be suitable for the purposes described herein.

Methods of obtaining VHHs that bind to a specific antigen or epitope have been described earlier in R. van der Linden et al., Journal of Immunological Methods, 240 (2000) 185-195; Li et al., J Biol Chem., 287 (2012) 13713-13721; Deffar et al., African Journal of Biotechnology Vol. 8 (12), pp. 2645-2652, 17 Jun. 2009; and WO94/04678.

VHH domains derived from camelids can be "humanized" (also termed "sequence-optimized" herein, "sequence-optimizing" may, in addition to humanization, encompass an additional modification of the sequence by one or more mutations that furnish the VHH with improved properties, such as the removal of potential post translational modification sites) by replacing one or more amino acid residues in the amino acid sequence of the original VHH sequence by one or more of the amino acid residues that occur at the corresponding position(s) in a VH domain from a conventional human 4-chain antibody. A humanized VHH domain can comprise one or more fully human framework region sequences.

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting are known in the art.

As used herein, the term "epitope" or the term "antigenic determinant" used interchangeably refers to any antigenic determinant on the antigen to which the paratope of an antibody binds. Antigenic determinants usually comprise chemically active surface groups of molecules, such as amino acids or sugar side chains, and usually have specific three-dimensional structural characteristics and specific charge characteristics. For example, an epitope usually includes at least 3, 4, 5, 6, 7, 8, 9, 10, 11, 12, 13, 14, or 15 consecutive or non-consecutive amino acids in a unique spatial conformation, which can be a "linear epitope" or a "conformational" epitope. See, for example, Epitope Mapping Protocols in Methods in Molecular Biology, Vol. 66, G. E. Morris, Ed. (1996). In the linear epitope, all interaction points between a protein and an interacting molecule (such as an antibody) exist linearly along the protein's primary amino acid sequence. In a conformational epitope, interaction points exist across protein amino acid residues that are separated from each other.

Many epitope mapping techniques well known in the art can be used to identify an epitope of a given antigen. See, for example, Epitope Mapping Protocols in Methods in Molecular Biology, Volume 66, G. E. Morris, Ed. (1996). For example, linear epitopes can be determined by, for example, the following method: synthesizing a large number of peptides on a solid support at the same time, wherein these peptides correspond to parts of the protein molecule, and reacting these peptides with antibodies while still attached to the support. These techniques are known in the art and are described in, for example, U.S. Pat. No. 4,708,871; Geysen et al. (1984) Proc. Natl. Acad. Sci. USA 81: 3998-4002; Geysen et al. (1986) Molec. Immunol. 23:709-715. Similarly, conformational epitopes can be identified by determining spatial configuration of amino acids, such as by, for example, x-ray crystallography and 2-dimensional nuclear magnetic resonance. See, for example, Epitope Mapping Protocols (ibid.).

Conventional techniques known to those skilled in the art can be used to screen antibodies for competitively binding to the same epitope. For example, competition and cross-competition studies can be conducted to obtain antibodies that compete with each other or cross-compete for binding to an antigen. A high-throughput method for obtaining antibodies that bind to the same epitope based on their cross-competition is described in international patent application WO03/48731. Therefore, conventional techniques known to those skilled in the art can be used to obtain antibodies and antigen-binding fragments thereof that compete with the antibody molecules of the invention for binding to the same epitope on PD-L1.

Generally, the term "specificity" refers to the number of different types of antigens or epitopes to which a particular antigen-binding molecule or antigen-binding protein (such as an immunoglobulin single variable domain of the invention) molecule can bind. The specificity of an antigen-binding molecule can be determined based on its affinity and/or avidity. The affinity, represented by the equilibrium constant (KD) for the dissociation of an antigen with an antigen-binding protein, is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person, affinity can be determined in a manner known per se, depending on the specific antigen of interest. Avidity is the measure of the strength of binding between an antigen-binding molecule (such as an immunoglobulin, an antibody, an immunoglobulin single variable domain or a polypeptide containing it) and the pertinent antigen. Avidity is related to both the affinity between an epitope and its antigen binding site on the antigen-binding molecule and the number of pertinent binding sites present on the antigen-binding molecule.

As used herein, the term "PD-L1 binding polypeptide" means any polypeptide capable of specifically binding to PD-L1, such as the single domain antibody of the invention that specifically binds to PD-L1.

"PD-L1 binding polypeptide" may refer to a monovalent polypeptide that binds to PD-L1 (i.e. a polypeptide that binds to one epitope of PD-L1), and a bivalent or multivalent binding polypeptide (i.e. a binding polypeptide that binds to more than one epitope). The "PD-L1 binding polypeptide" of the invention may comprise at least one immunoglobulin single variable domain, such as VHH, that binds to PD-L1.

Generally, the PD-L1 binding polypeptide of the invention will bind to the antigen to be bound (i.e., PD-L1) with a dissociation constant (KD) of preferably $10^{-7}$ to $10^{11}$ mol/L(M), more preferably $10^{-8}$ to $10^{-11}$ mol/L, or even more preferably $10^{-9}$ to $10^{-11}$, even more preferably $10^{-10}$ to $10^{-11}$ M or lower as measured in the Biacore or KinExA assay and/or an association constant (KA) of at least $10^7 M^{-1}$, preferably at least $10^8 M^{-1}$, more preferably at least $10^9 M^{-1}$, more preferably at least $10^{10} M^{-1}$, for example at least $10^{11} M^{-1}$. Any of KD values greater than $10^{-4}$ M is generally considered to indicate non-specific binding. The specific binding of an antigen binding protein to an antigen or epitope can be determined in any suitable manner known, including, for example, a surface plasmon resonance (SPR) assay, a Scatchard assay, and/or a competitive binding assay described herein (e.g., a radioimmunoassay (RIA), an enzyme immunoassay (EIA) and a sandwich competition assay).

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp or into Phe; Val into Ile or into Leu.

"Sequence identity" between two polypeptide sequences refers to percentage of identical amino acids between the sequences. "Sequence similarity" refers to percentage of amino acids that are identical or represent substitutions of conservative amino acids. Methods for evaluating degree of sequence identity between amino acids or nucleotides are known to those skilled in the art. For example, amino acid sequence identity is usually measured using a sequence analysis software. For example, the BLAST program of the NCBI database can be used to determine the identity. For the determination of sequence identity, see, for example: Computational Molecular Biology, Lesk, AM, ed., Oxford University Press, New York, 1988; Biocomputing: Informatics and Genome Projects, Smith, D W, ed., Academic Press, New York, 1993; Computer Analysis of Sequence Data, Part I, Griffin, A M, and Griffin, HG, eds., Humana Press, New Jersey, 1994; Sequence Analysis in Molecular Biology, von Heinje, G., Academic Press, 1987 and Sequence Analysis Primer, Gribskov, M. and Devereux, J., eds., M Stockton Press, New York, 1991.

A polypeptide or nucleic acid molecule is regarded as "substantially isolated" when it has been isolated from at least one other components that are normally associated with it in its natural biological sources or media (culture medium) from which the polypeptide or nucleic acid molecule is obtained (such as another protein/polypeptide, another nucleic acid, another biological component or macromolecule or at least one contaminant, impurity or trace component), compared with the sources or/and the media (culture mediums). In particular, the polypeptide or nucleic acid molecule is regarded as "substantially isolated" when it has been purified at least 2 times, especially at least 10 times, more especially at least 100 times and up to 1000 times or more. As determined by suitable techniques (e.g. suitable chromatographic techniques, such as polyacrylamide gel electrophoresis), the "substantially isolated" polypeptide or nucleic acid molecule is preferably substantially homogeneous.

The term "subject" as used herein means a mammal, especially a primate, especially a human.

PD-L1 Binding Polypeptide of the Invention

In one aspect, the invention provides a programmed death ligand 1 (PD-L1) binding polypeptide, characterized by being capable of specifically binding PD-L1 and comprising at least one immunoglobulin single variable domain, wherein the at least one immunoglobulin single variable domain comprises:

CDR1, which comprises an amino acid sequence set forth in SEQ ID NO: 5 or an amino acid sequence having one or more amino acid residue substitutions, deletions or additions compared to SEQ ID NO: 5, CDR2, which comprises an amino acid sequence set forth in SEQ ID NO: 6 or an amino acid sequence having one or more amino acid residue substitutions, deletions or additions compared to SEQ ID NO: 6, for example, comprises an amino acid sequence set forth in SEQ ID NO: 13, and CDR3, which comprises an amino acid sequence set forth in SEQ ID NO: 7 or an amino acid sequence having one or more amino acid residue substitutions, deletions or additions compared to SEQ ID NO: 7.

In some specific embodiments, the at least one immunoglobulin single variable domain comprises:

CDR1, which comprises the amino acid sequence set forth in SEQ ID NO: 5,

CDR2, which comprises the amino acid sequence set forth in SEQ ID NO: 13, and

CDR3, which comprises the amino acid sequence set forth in SEQ ID NO:7.

In some embodiments, the immunoglobulin single variable domain comprises an amino acid sequence that is at least 80%, preferably at least 90%, more preferably at least 95%, even more preferably at least 99% identical to the amino acid sequence of SEQ ID NO:1.

In some embodiments, the immunoglobulin single variable domain is derived from SEQ ID NO:1. The polypeptide of SEQ ID NO:1 comprises a total of 3 lysine residues with free amino group (at positions 64, 75 and 86 of SEQ ID NO:1, respectively), and these groups can be used for conjugation of a chelating agent such as NOTA. In order to optimize the purity of the conjugate of the binding polypeptide and the chelating agent such as NOTA, and to ensure that 1 molar of the polypeptide can and can only be conjugated with 1 molar of the chelating agent, these lysine residues can be substituted. For example, in some preferred embodiments, the immunoglobulin single variable domain can comprise only one lysine residue.

In addition, when lysine residues are substituted, in order to retain suitable binding ability, adjacent residues of the lysine residues can be mutated. For example, in some embodiments, the immunoglobulin single variable domain comprises a K64Q substitution compared to SEQ ID NO:1. In some embodiments, the immunoglobulin single variable domain comprises K86R and P87A substitutions compared to SEQ ID NO:1. In some embodiments, the immunoglobulin single variable domain comprises H71R, R73N, A74S, and K75E substitutions compared to SEQ ID NO:1. In some embodiments, the immunoglobulin single variable domain comprises R73N and K75E substitutions compared to SEQ ID NO:1. In some embodiments, the immunoglobulin single variable domain comprises K64Q, H71R, R73N, A74S, and K75E substitutions compared to SEQ ID NO:1. Experiments in this application show that such mutations do not destroy the binding affinity to PD-L1, even when they are located in the CDRs (such as K64Q). The numbering of amino acid position herein refer to SEQ ID NO:1.

When the term "comprise" is used herein to describe a sequence of a protein or nucleic acid, the protein or nucleic acid may consist of the sequence, or may have additional amino acids or nucleotides at either or both ends of the protein or nucleic acid, but still has the activity described in the invention. For example, the PD-L1 binding polypeptide of the invention may also comprise a tag suitable for expression and/or purification, including but not limited to a His tag.

In some embodiments, the immunoglobulin single variable domain comprises an amino acid sequence selected from the group consisting of SEQ ID NO: 1-2, 8-12, and 18-22.

In some embodiments, the immunoglobulin single variable domain is VHH.

In some embodiments, the PD-L1 binding polypeptide does not block binding of PD-1 to PD-L1. Potential side effects can be reduced by not blocking the binding of PD-1 and PD-L1 to avoid affecting the normal function of PD-L1. In addition, the epitope of PD-1 to which the PD-L1 binding polypeptide of the invention binds is different from the binding sites of PD-L1 in the prior art to which PD-1 binds, so the PD-L1 binding polypeptide of the invention may not affect efficacy of other antibodies designed to block the interaction between PD-1 and PD-L1, such as therapeutic antibodies. Therefore, in some embodiments, the PD-L1 binding polypeptide of the invention does not block the interaction of the therapeutic antibody against PD-L1 with PD-L1, thereby enabling to treat a cancer by administering a therapeutic antibody against PD-L1 and to monitor the cancer simultaneously using the PD-L1 binding polypeptide of the invention or conjugated molecules derived therefrom.

Nucleic Acid, Vector, Host Cell

In another aspect, the invention involves a nucleic acid molecule encoding the PD-L1 binding polypeptide of the invention. The nucleic acid of the invention may be RNA, DNA or cDNA. Those skilled in the art may select nucleic acid molecules encoding the PD-L1 binding polypeptide according to needs or conventional means.

The nucleic acids of the invention may also be in the form of a vector, which may be present in the vector and/or may be part of a vector such as a plasmid, a cosmid or YAC. The vector may especially be an expression vector, i.e., a vector that provides expression of the PD-L1 binding polypeptide in vitro and/or in vivo (i.e., in a suitable host cell, host organism, and/or expression system). The expression vector typically comprises at least one nucleic acid of the invention operably linked to one or more suitable expression regulatory elements (e.g., promoters, enhancers, terminators, etc.). Selection of the elements and their sequences for expression in a particular host is common knowledge to those skilled in the art. Specific examples of regulatory elements and other elements useful or essential for the expression of the PD-L1 binding polypeptides of the invention include, such as promoters, enhancers, terminators, integration factors, selection markers, leader sequences, reporter genes.

The nucleic acids of the invention may be prepared or obtained in a known manner (for example by automated DNA synthesis and/or recombinant DNA techniques) based on information about the amino acid sequence of the polypeptides of the invention disclosed herein, and/or may be isolated from a suitable natural sources.

In another aspect, the invention involves a host cell that expresses or is capable of expressing one or more of the PD-L1 binding polypeptides of the invention and/or comprises a nucleic acid or vector of the invention. Preferred host cells of the invention are bacterial cells, fungal cells or mammalian cells.

Suitable bacterial cells include cells of Gram-negative bacterial strains (e.g., *Escherichia coli* strains, *Proteus* strains, and *Pseudomonas* strains) and Gram-positive bacterial strains (e.g., *Bacillus* strains, *Streptomyces* strains, *Staphylococcus* strains, and *Lactococcus* strains.

Suitable fungal cells include cells of the species of *Trichoderma, Neurospora,* and *Aspergillus*; or include cells of the species of *Saccharomyces* (e.g., *Saccharomyces cerevisiae*), *Schizosaccharomyces* (e.g. *Schizosaccharomyces pombe*), *Pichia* (e.g. *Pichia pastoris* and *Pichia methanolica*) and *Hansenula*.

Suitable mammalian cells include, for example, HEK293 cells, CHO cells, BHK cells, HeLa cells, COS cells, and the like.

However, amphibian cells, insect cells, plant cells, and any other cells in the art for expressing a heterologous protein can also be used in the invention.

The invention also provides a method of producing a PD-L1 binding polypeptide of the invention, generally comprising the steps of:
    culturing the host cell of the invention under conditions allowing the expression of the PD-L1 binding polypeptide of the invention; and
    recovering the PD-L1 binding polypeptide expressed by the host cell from the culture; and
    optionally further purifying and/or modifying the PD-L1 binding polypeptide of the invention.

The PD-L1 binding polypeptide of the invention may be produced in an intracellular manner (e.g., in the cytoplasm, in the periplasm, or in inclusion bodies) in cells as described above, followed by isolation from the host cells and optionally further purification; or it may be produced in an extracellular manner (for example in the medium in which the host cells are cultured), followed by isolation from the medium and optionally further purification.

Methods and reagents for recombinant production of polypeptides, such as specific suitable expression vectors, transformation or transfection methods, selection markers, methods for inducing protein expression, culture conditions, and the like, are known in the art. Similarly, protein isolation and purification techniques suitable for the methods of making the PD-L1 binding polypeptides of the invention are well known to those skilled in the art.

However, the PD-L1 binding polypeptide of the invention can also be obtained by other methods of protein production known in the art, such as chemical synthesis, including solid phase or liquid phase synthesis.

Conjugated Molecules

In another aspect, the invention provides a conjugated molecule containing a PD-L1-binding polypeptide of the invention, and at least one detectable marker conjugated to the pD-L1-binding polypeptide of the invention.

The detectable marker includes, but is not limited to, radionuclides, fluorescent agents, chemiluminescent agents, bioluminescent agents, paramagnetic ions, and enzymes.

Fluorescent agents that can be used for conjugation include, but are not limited to, fluorescein isothiocyanate, rhodamine, phycoerythrin, phycocyanin, allophycocyanin, o-phthalaldehyde, and fluorescamine. Chemiluminescent agents that can be used for conjugation include, but not limited to luminol, isoluminol, aromatic acridinium esters, imidazoles, acridine salts and oxalates. Bioluminescent agents that can be used for conjugation include, but are not limited to, luciferin, luciferase, and jellyfish luminescence protein. Paramagnetic ions that can be used for conjugation include, but are not limited to, chromium (III), manganese (II), iron (III), iron (II), cobalt (II), nickel (II), copper (II), neodymium (III), samarium(III), ytterbium(III), gadolinium (III), vanadium(II), terbium(III), dysprosium(III), holmium (III) and erbium(III), or radiopaque materials, such as dam, diatrizoate, ethiodized oil, gallium citrate, iocarmic acid, locetamic acid, iodamide, odipamide, lodoxamic acid, Iopromide, iohexol, iopamidol, Iopanoic Acid, ioprocemic acid, iosefamic acid, ioseric acid, locarmic Acid, lotasul, iotetric acid, iothalamic acid, iotroxic acid, ioxaglic acid, ioxotrizoic acid, ipodate, meglumine, metrizamide, metrizoic salts, dionosil, and thallous hydroxide. Enzymes that can be used for conjugation include, but are not limited to, horseradish peroxidase and the like.

Preferably, the detectable marker is a radionuclide. The radionuclide that can be used for conjugation is, for example, a radionuclide with energy between 20-4000 KeV, including but not limited to $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{68}$Ge, $^{86}$Y, $^{90}$Y, $^{89}$Zr, $^{94m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr or other γ-, β-, or positron emitters. In some embodiments, the detectable marker is $^{68}$Ga or $^{125}$I.

Methods of conjugating a detectable marker to a polypeptide are well known to those skilled in the art. For example, in some embodiments, the PD-L1 binding polypeptide may be conjugated to a detectable marker via a chelating agent.

In order to label the PD-L1 binding polypeptide of the invention with a radionuclide such as $^{68}$Ga, the PD-L1 binding polypeptide of the invention can be reacted with a reagent having a long tail that is attached with a plurality of integration groups for binding to ions. Such tails can be, for example, polylysine, polysaccharides, or other polymers with derivatized or derivatizable chain of side groups that can bind to chelating groups, such as ethylenediaminetetraacetic acid (EDTA), diethylenetriaminepentaacetic acid (DTPA), DOTA (1,4,7,10-tetraazacyclododecane-1,4,7,10-tetraacetic acid), NOTA, TETA, NETA, porphyrin, polyamine, crown ether, bisthiosemicarbazone, polyoxime and similar groups that are known to be useful for this purpose. A chelating agent can be attached to an antibody using standard chemical methods. In some embodiments, the detectable marker is conjugated to the PD-L1 binding polypeptide of the invention via a chelating agent. The chelating agent used includes but is not limited to NOTA, DOTA, TETA or NETA.

In some specific embodiments, the detectable marker is $^{68}$Ga and the chelating agent is NOTA. In some embodiments, the PD-L1 binding polypeptide comprises the amino acid sequence set forth in SEQ ID NO: 12 or 22.

In another aspect, the invention provides a method for manufacturing a conjugated molecule labeled with the radionuclide of the invention, such as $^{68}$Ga, which comprises 1) conjugating the PD-L1 binding polypeptide of the invention with a chelating agent to generate a conjugate of the PD-L1 binding polypeptide and the chelating agent; and 2) contacting the product of step 1) with the radionuclide such as $^{68}$Ga, whereby labeling the PD-L1 binding polypeptide of the invention with the radionuclide such as $^{68}$Ga through chelating effect of the chelating agent. In some embodiments, the chelating agent is NOTA, and in step 1), the PD-L1 binding polypeptide is reacted with p-SCN-Bn-NOTA or p-NH2-Bn-NOTA to generate the conjugate of PD-L1 binding polypeptide and NOTA.

In another aspect, the invention provides a method for manufacturing the $^{125}$I-labeled conjugated molecule of the invention, which comprises 1) reacting the PD-L1 binding polypeptide of the invention with $^{125}$I in the presence of chloramine T; and 2) optionally, terminating the reaction with sodium metabisulfite.

Detecting/Diagnostic Uses

In another aspect, the invention provides a method for detecting the presence of PD-L1 and/or the expression level of PD-L1 in a biological sample, comprising:

a) contacting the biological sample and the control sample with the PD-L1 binding polypeptide of the invention and/or the conjugated molecule of the invention under the condition that the PD-L1 binding polypeptide of the invention and/or the conjugated molecule of the invention can form a complex with PD-L1; and b) detecting the complex formation, wherein difference in the complex formation between the biological sample and the control sample is indicative of the presence of PD-L1 and/or the expression level of PD-L1 in the sample. In some embodiments, the biological sample is an ex vivo sample.

In another aspect, the invention provides a composition comprising the PD-L1 binding polypeptide of the invention and/or the conjugated molecule of the invention, and optionally a physiologically acceptable carrier. The composition can be used as a diagnostic agent, for example, a diagnostic agent for detecting and/or diagnosing PD-L1 related diseases.

In another aspect, the invention provides a diagnostic agent for detecting and/or diagnosing PD-L1 related diseases such as cancers, comprising the PD-L1 binding polypeptide of the invention and/or the conjugated molecule of the invention, and optionally a physiologically acceptable carrier. In some embodiments, the diagnostic agent is a contrast agent.

The PD-L1 binding polypeptide of the invention and/or the conjugated molecule of the invention is particularly suitable for in vivo imaging, for example, for Emission Computed Tomography (ECT). For example, the PD-L1 binding polypeptide of the invention and/or the conjugated molecule of the invention can be applied to Single-Photon Emission Computed Tomography (SPECT) and Positron Emission Tomography (PET) depending on various markers. In tumor diagnosis, high-resolution tumor imaging can be provided and quantitative analysis can be performed with the images. The SPECT imaging may also include SPECT/CT imaging, and the PET imaging may also include PET/CT imaging, which can provide improved imaging effects.

Therefore, in some embodiments, the contrast agent is an ECT contrast agent, such as a SPECT contrast agent or a PET contrast agent.

In another aspect, the invention provides use of the PD-L1 binding polypeptide of the invention and/or the conjugated molecule of the invention in manufacturing a diagnostic agent for detecting and/or diagnosing PD-L1 related diseases such as cancers. In some embodiments, the diagnostic agent is a contrast agent. In some embodiments, the contrast agent is an ECT contrast agent, such as a SPECT contrast agent or a PET contrast agent In another aspect, the invention provides a method for detecting and/or diagnosing PD-L1 related diseases such as cancers in a subject, comprising administering to the subject the PD-L1 binding polypeptide of the invention and/or the conjugated molecule of the invention and/or the diagnostic agent of the invention.

In some embodiments, the method further includes the step of conducting imaging to the subject, such as ECT imaging. In some embodiments, the ECT imaging is SPECT imaging. In some embodiments, the ECT imaging is PET imaging. The imaging techniques and devices used for scanning by SPECT or PET are well known in the art and any such well-known ECT imaging techniques and devices can be used.

Diseases that can be detected and/or diagnosed by the PD-L1 binding polypeptide of the invention and/or the conjugated molecules of the invention and/or the diagnostic agents of the invention include diseases with abnormally elevated PD-L1 expression in cells, tissues or organs, such as infectious diseases, cancers, etc.

Preferred cancers which may be detected and/or diagnosed using the PD-L1 binding polypeptide of the invention highly express PD-L1. Non-limiting examples include lung cancer, ovarian cancer, colon cancer, rectal cancer, melanoma (e.g., metastatic malignant melanoma), bladder cancer, breast cancer, liver cancer, lymphoma, hematological malignancy, head and neck cancer, glioma, gastric cancer, nasopharyngeal cancer, laryngeal cancer, cervical cancer, corpus carcinoma, and osteosarcoma. Examples of other cancers which may be detected and/or diagnosed using the PD-L1 binding polypeptide of the invention include bone cancer, pancreatic cancer, skin cancer, prostatic cancer, cutaneous or intraocular malignant melanoma, uterine cancer, cancer of the anal region, testicular cancer, carcinoma of the fallopian tubes, carcinoma of the endometrium, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the ureter, neoplasm of the central nervous system (CNS), primary CNS lymphoma, tumor angiogenesis, spinal axis tumor, brain stein glioma, pituitary adenoma, Kaposi's sarcoma, epidermoid cancer, squamous cell cancer, T-cell lymphoma, environmentally induced cancers including those induced by asbestos, and combinations of said cancers. The invention is also useful for the detection and/or diagnosis of metastatic cancer, particularly metastatic carcinoma expressing PD-L1 (Iwai et al. (2005) Int Immunol 17: 133-144).

In another aspect, the invention provides a kit comprising the PD-L1 binding polypeptide of the invention and/or the conjugated molecules of the invention and/or the diagnostic agents of the invention. The kit is used to implement the method of the invention. The kit typically includes a label indicating the intended use of the contents of the kit. The term label includes any written or recorded material provided on or with the kit or otherwise provided with the kit.

EXAMPLES

Hereinafter, the invention will be further described by way of examples, but the invention is not limited to the scope of the described examples.

Example 1: Screening for Heavy Chain Single Domain Antibodies Against PD-L1

1.1 Library Construction

The PDL1-Fc fusion protein for immunization was expressed in CHO cells and purified by Protein A affinity chromatography. A Xinjiang Bactrian camel was chosen for immunity. After 4-times immunizations, 100 ml of camel peripheral blood lymphocytes was withdrawn and a total RNA was extracted using a RNA extraction kit provided by QIAGEN. The extracted RNA was reversely transcribed into cDNA using a Super-Script III FIRST STRANDSUPERMIX kit (Thermo Fisher Scientific) according to the instructions. The nucleic acid fragment encoding the variable region of the heavy chain antibody was amplified by a nested PCR:

The first round of PCR:

```
Upstream primer:
                            (SEQ ID NO: 14)
GTCCTGGCTGCTCTTCTACAAGGC;

Downstream primer:
                            (SEQ ID NO: 15)
GGTACGTGCTGTTGAACTGTTCC.
```

The second round of PCR:
The products from the first round of PCR as templates,

```
Upstream primer:
                            (SEQ ID NO: 16)
GATGTGCAGCTGCAGGAGTCTGGRGGAGG;

Downstream primer:
                            (SEQ ID NO: 17)
GGACTAGTGCGGCCGCTGGAGACGGTGACCTGGGT.
```

The nucleic acid fragment of the target heavy-chain single domain antibody was recovered, and cloned into a vector pCDisplay-3 (Creative Biolabs, Cat: VPT4023) for phage display using restriction enzymes PstI and NotI. The product was subsequently electrotransformed into electroporation-competent E. coli TG1 cells to construct and verify a phage display library of heavy-chain single domain antibodies against PD-L1. The library capacity calculated by gradient dilution followed by plating is $1.33 \times 10^8$. To detect an insertion rate of the library, 24 clones were randomly selected for colony PCR. The results demonstrated that the insertion rate has reached 100%.

1.2 Screening for Heavy Chain Single Domain Antibodies Against PD-L1

The plate was coated with the PDL1-Fc fusion protein in 10 µg/well and placed overnight at 4° C. The next day, 1% skimmed milk was used for blocking for 2 hours at room temperature, and 100 µl of phage (8×10$^{11}$ tfu, from the phage display library of camel heavy-chain single domain antibody constructed in 1.1) was added and incubated at room temperature for 1 hour and then washed with PBST (0.05% Tween 20 in PBS) 5 times to wash off unbound phages. Finally, the phages that specifically bind to PD-L1 were dissociated using triethylamine (100 mM) and used to infect *E. coli* TG1 at the logarithmic growth phase to produce and purify the phages for the next round of screening. The same screening process was repeated for 3-4 rounds. As a result, positive clones were enriched, thereby achieving the purpose of screening for PD-L1 specific antibodies in the antibody library using the phage display technology.

1.3 Screening for Single Specific Positive Clone Using Enzyme-Linked Immunosorbent Assay (ELISA) of Phage After 3-4 rounds of screening, the obtained PD-L1 binding positive phages were used to infect empty *E. coli* cells and plated. 96 single colonies were then selected and cultured separately to produce and purify the phages. The plate was coated with the PDL1-Fc fusion protein at 4° C. overnight, the obtained sample phages (the control group: blank phages) were added, and incubated at room temperature for 1 hour. After washing, the primary antibody, mouse anti-HA tag antibody (purchased from Beijing Kangwei Century Biotechnology Co., Ltd.), was added and incubated at room temperature for 1 hour. After washing, the secondary antibody, goat anti-mouse alkaline phosphatase labeled antibody (purchased from Amictech Technology Co., Ltd.), was added and incubated at room temperature for 1 hour. After washing, the developing solution of alkaline phosphatase was added and absorption values were read at wavelength of 405 nm. When the OD value for the sample well is 3 times greater than the OD value for the control well, the sample well is determined as a positive clone well. The bacterium in the positive clone well were transferred to LB liquid containing 100 µg/mL ampicillin for culture in order to extract plasmids and perform the sequence analysis.

The sequence of protein of each clone was analyzed according to the sequence alignment software Vector NTI. The clones with the same CDR1, CDR2, and CDR3 sequences are regarded as the same antibody, and the clones with different CDR sequences are regarded as different antibodies. Finally, a PD-L1 heavy-chain single domain antibody was obtained, which was named as 109.

Example 2: Preliminary Evaluation and Identification of the Heavy Chain Single Domain Antibodies Against PD-L1

2.1 Construction of Gene Clones of PD-L1 Single Domain Antibody

The amino acid sequence of the single domain antibody is set forth in Table 1, wherein 109-chis is a recombinant protein with a His tag at C-terminal. The CDR sequences are shown in boxes.

TABLE 1

| Protein names | SEQ ID NO | Sequences |
|---|---|---|
| 109 | 1 | QVQLQESGGGSVQAGGSLRLSCTAS GFSLDDSDMGWYRQARGNVCQLVS TIASDRSTYYTPSVKGRFTISHDR AKNTIYLQMNSLKPEDTAVYYCAA APRLAYTTAMTCEGDFAYWGQGTQ VTVSS |
| 109-chis | 2 | QVQLQESGGGSVQAGGSLRLSCTAS GFSLDDSDMGWYRQARGNVCQLVST IASDRSTYYTPSVKGRFTISHDRAK NTIYLQMNSLKPEDTAVYYCAAAPR LAYTTAMTCEGDFAYWGQGTQVTVS SGSMDPGGSHHHHHHHH |

The nucleotide sequences encoding the single domain antibodies of Table 1 are set forth in SEQ ID NO:3 and SEQ ID NO:4.

The nucleotide sequence of 109 single domain antibody:

(SEQ ID NO: 3)
CAGGTGCAGCTGCAGGAGTCTGGAGGAGGCTCGGTGCAGGCTGGGGGGT

CTCTGAGACTCTCCTGTACAGCCTCTGGATTCAGTTTAGATGATTCTGA

CATGGGCTGGTACCGCCAGGCTCGTGGGAATGTGTGCCAGTTGGTGTCA

ACAATTGCTAGTGATAGAAGTACATACTATACACCCTCCGTGAAGGGCC

GATTCACCATCTCCCATGACAGAGCCAAGAACACAATTTATCTGCAAAT

GAACAGCCTGAAACCTGAGGACACGGCCGTGTATTACTGTGCGGCAGCC

CCTCGCCTGGCCTACACAACGGCGATGACGTGCGAGGGGGACTTTGCTT

ACTGGGGCCAGGGAACCCAGGTCACCGTCTCCTCATAA.

The nucleotide sequence of 109-chis:

(SEQ ID NO: 4)
CAGGTGCAGCTGCAGGAGTCTGGAGGAGGCTCGGTGCAGGCTGGGGGGT

CTCTGAGACTCTCCTGTACAGCCTCTGGATTCAGTTTAGATGATTCTGA

CATGGGCTGGTACCGCCAGGCTCGTGGGAATGTGTGCCAGTTGGTGTCA

ACAATTGCTAGTGATAGAAGTACATACTATACACCCTCCGTGAAGGGCC

GATTCACCATCTCCCATGACAGAGCCAAGAACACAATTTATCTGCAAAT

GAACAGCCTGAAACCTGAGGACACGGCCGTGTATTACTGTGCGGCAGCC

CCTCGCCTGGCCTACACAACGGCGATGACGTGCGAGGGGGACTTTGCTT

ACTGGGGCCAGGGAACCCAGGTCACCGTCTCCTCAGGCAGCATGGATCC

TGGAGGATCTCATCATCACCACCACCATCATCACTAA.

The CDR sequences of the 109 antibody are: CDR1: GFSLDDSDMG (SEQ ID NO: 5); CDR2: IASDRSTYYTPSVKG (SEQ ID NO: 6); and CDR3: APRLAYTTAMTCEGDFAY (SEQ ID NO: 7).

PCR amplification was performed using the primers designed based on the nucleotide sequences of the single domain antibodies and the synthetic DNAs of whole gene as a template. The PCR products were cloned into pCDNA4 (Invitrogen, Cat V86220) vectors and subjected to gene sequence analyses to determine correctness of the gene sequences of the target clones.

2.2 Preparation of PD-L1 Antibody Protein with Mammalian Cells

The recombinant constructed plasmid of the single domain antibody fusion protein was transfected into HEK293 cells for antibody expression. The recombinant expression plasmids were diluted with Freestyle293 medium (Thermo Fisher Scientific, Art. No. 12338018) and added to the PEI (polyethyleneimine) solution required for transformation. The plasmid/PEI mixture was added to the HEK293 cell suspension and cultured at 37° C. and 10% $CO_2$ at 90 rpm. after 4 hours, the culture was supplemented with EX293 medium (Sigma, Art. No. 14571C) and 2 mM glutamine and cultured at 135 rpm. After 24 hours, the culture was added with 3.8 mM valproic acid VPA (Sigma, Art. No. P4543). After 5-6 days of culture, the supernatant from the transient expression culture was collected, and the 109-chis single domain antibody was purified by Ni+ resin gel affinity chromatography to obtain a purified antibody with a purity of up to 95% or more measured by an SDS-PAGE electrophoresis. 109 single domain antibody was firstly enriched in one-step by affinity chromatography, and then purified by ion chromatography column to obtain purified 109 antibody with a purity of up to 95% or more measured by an SDS-PAGE electrophoresis (as shown in FIG. 1A-C).

2.3 Detection of Specific Binding of PD-L1 Heavy-Chain Single Domain Antibody to Human PD-L1 Protein PDL1-Fc fusion protein was transiently expressed by HEK293 and purified by nickel column affinity chromatography. The plate was coated with the obtained PDL1-Fc fusion protein in 0.5 μg/well overnight at 4° C., and then added to the serial diluted obtained PD-L1 single domain antibody protein and incubated at room temperature for 1 hour. After washing, anti-his-horseradish peroxidase (HRP) labeled antibody (purchased from Abcam, Art. No. ab1187) was added and incubated at room temperature for 1 hour. After washing, the developing solution was added, and absorption values were read at wavelength of 405 nm. The data processing and mapping analysis were performed using software SotfMaxPro v5.4. through four-parameter fitting, the binding curve and EC50 value (2.891 ng/mL) of antibody-to-PD-L1 as shown in FIG. 2 are obtained, which reflects the affinity of the 109 antibody to PD-L1.

Example 3: In Vitro Activity Analysis of PD-L1 Antibody Protein 3.1 Competitive ELISA to Investigate Blocking Effect of PD-L1 Heavy-Chain Single Domain Antibody on Interaction Between PD-1 and PD-L1

PDL1-muFc fusion protein (using mouse Fc) and PD1-Fc fusion protein were obtained by being cloned into pCDNA4 vector (Invitrogen, Cat V86220) and expressed in HEK293 cells. The plate was coated with PDL1-muFc fusion protein in 0.5 jag/well overnight at 4° C., and then 10 μg PD1-Fc was added to each of wells (the control group: no antibody or protein was added, and only an equal volume of buffer was added) with 3 μg/L of the initial dilution concentration for the heavy-chain single domain antibody, 109-chis (the control group: the buffer), in 2 times dilution, with 12 gradients, and incubated at room temperature for 1 hour. After that, anti-his-HRP (purchased from Abcam company) was added and incubated at room temperature for 1 hour. The developing solution was then added, and absorption values were read at wavelength of 405 nm. In the presence of excess PD-1, if it tends to show an S-curve binding for the binding as the concentration of the heavy-chain single domain antibody, 109-chis, was increased, it is considered that the antibody has no blocking effect.

The plate was coated with PDL1-muFc fusion protein in 0.5 μg/well overnight at 4° C., and then 10 μg PD1-Fc was added to each of wells (the control group: no antibody or protein was added, and only an equal volume of buffer was added) with 3 μg/L of the initial dilution concentration for the heavy-chain single domain antibody, 109-chis (the control group: the buffer), in 2 times dilution, with 12 gradients, and incubated at room temperature for 1 hour. After that, anti-Fc-HRP (purchased from Abcam company) was added and incubated at room temperature for 1 hour. The developing solution was then added, and absorption values were read at wavelength of 405 nm. If as the concentration of the heavy-chain single domain antibody, 109-chis, was increased, the binding to PD-1 trends to be stable, it is considered that the binding of PD-1 to PDL1 is not affected by the presence of the antibody. The results are shown in FIG. 3A, the epitope of 109 binding to PDL1 is not the same as that of PD-1, thereby not affecting the binding of 109 protein to PD-L1 protein by the presence of PD-1 protein.

3.2 Detection of Binding Effect of PD-L1 Heavy-Chain Single Domain Antibody on Cell Surface PD-L1 by Flow Cytometry A375 cells that stably express the human PD-L1 protein on the membrane (A375-PDL1 cells) were obtained by constructing human melanoma A375 cells stably transfected with the gene of human PD-L1 full-length protein. The tumorigenic cell line, MCF-7, that does not express PD-L1 was used as a negative control. The MCF-7 cell line was obtained from the American Type Culture Collection (ATCC) with the deposit number ATCC HTB-22, and was cultured as recommended. The cells were cultured to >90% confluence before use. The anti-PD-L1 single domain antibody, 109, was used for the flow cytometric analysis of these cell lines for quantitative analysis of indirect immunofluorescence staining to determine the number of surface receptors for each cell.

The cell dissociation buffer (PBS+10 mM EDTA) instead of trypsin was used to elute adherent cells from the cell culture dish to avoid proteolysis of cell surface receptors. The cells were washed twice in PBS, and resuspended in ice-cold buffer (PBS+0.5% BSA w/v) to a concentration of $5-10\times10^6$ cells/ml. an aliquot of 100 μL cells was mixed with 5 μg of the primary antibody and was incubated on ice for 45 minutes. The cells were then washed with 1 ml of the ice-cold flow cytometry buffer (PBS containing 2% bovine serum albumin), centrifuged at 300×g for 5 minutes, and resuspended in 0.5 μL of the buffer. 100 μL of 1:50 diluted solution of the secondary antibody-PE conjugate and PBS was added and incubated on ice in the dark for 45 minutes. The cells were then washed twice with 1 mL of the ice-cold buffer, centrifuged at 300×g for 5 minutes, and resuspended in 500 μL of the buffer.

The flow cytometric analysis was performed on the Beckman Coulter Cytomics FC500 MPL. For each of the tubes, a minimum of 5×104 events were collected. All analyses are in single color, and PE is detected in FL1. The forward scatter (FS) and side scatter (SS) data demonstrate that all of cell populations are clustered closely.

Figure 3B:
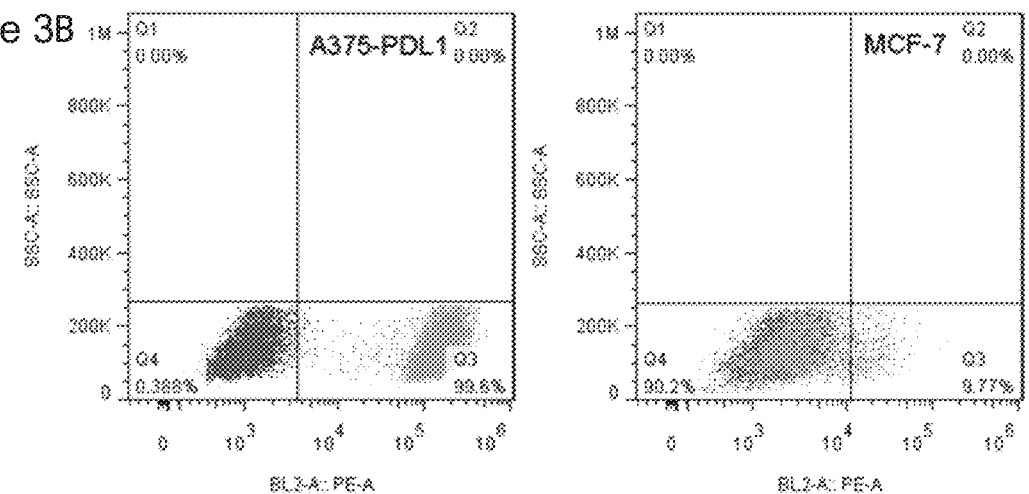

The flow cytometry was used to evaluate the PDL1 expression of cells in vitro (as shown in FIG. 3B). It shows the highest expression level of PDL1 for A375-PDL1 cells and almost no PDL1 expression for MCF-7 cells.

3.3 Identification of Binding Ability of PD-L1 Single Domain Antibody Protein to PD-L1 (Biacore)

The experimental temperature of Biacore was 25° C. and the injection flow rate was 50 μl/min. The analyte was diluted with the HBS-EP+ buffer to a certain concentration, and was allowed to flow through the blank reference channel and the activated channel in turn. The signal value generated on the blank reference channel reflects the non-specific adsorption of the analyte on the chip, and the signal value generated on the activated channel reflects the specific binding between the analyte and the ligand. The analyte was introduced for 300 s, and then the HBS-EP+ buffer was introduced for 180 s to dissociate the analyte from the ligand. 109 antibody was diluted with 7 gradients to 200 ng/ml, 100 ng/ml, 50 ng/ml, 25 ng/ml, 12.5 ng/ml, 6.25 ng/ml, 3.125 ng/ml. Different concentrations of analytes are repeatedly introduced and dissociated.

The data recorded by Biacore T200 is analyzed by the Biacore T200 Evaluation Software.

The results of the measured binding affinity of the anti-PD-L1 antibody are shown in Table 2. Its KD value is 1.7 nM. The results demonstrated that 109 protein has significant affinity for the PD-L1 target protein.

TABLE 2

| Binding affinity of 109 antibody to PD-L1 | |
|---|---|
| Ka | $2.534 \times 10^5 M^{-1} s^{-1}$ |
| Kd | $4.382 \times 10^{-4} s^{-1}$ |
| KD | $1.729 \times 10^{-9} M$ |

3.4 Immunohistochemistry

In vivo studies were carried out with female nude mice aged 6-8 weeks. Nude mice are raised in a specific pathogen (SPF)-free environment, with free access to food and water, and a standard 12-hour day-night lighting cycle. For heterotransplantation, 100 μl of cells (A375-PDL1 or MCF-7)/PBS were implanted subcutaneously in the right front leg of the mice. The cell inoculation density is about $5-6 \times 10^6$ cells/mouse. The implantation was performed under isoflurane anesthesia. Under these conditions, in more than 80% of injected animals, usable tumors (A375-PDL1 or MCF-7) (100-300n) were obtained after 3 to 4 weeks. Tumors were collected from mice by dissection, and the entire tumor was fixed with formalin and stored at 4° C. until immunohistochemistry. The immunohistochemical sections were prepared according to conventional methods well known to those skilled in the art and stained with anti-his-horseradish peroxidase (HRP) labeled antibody.

Figure 3C:
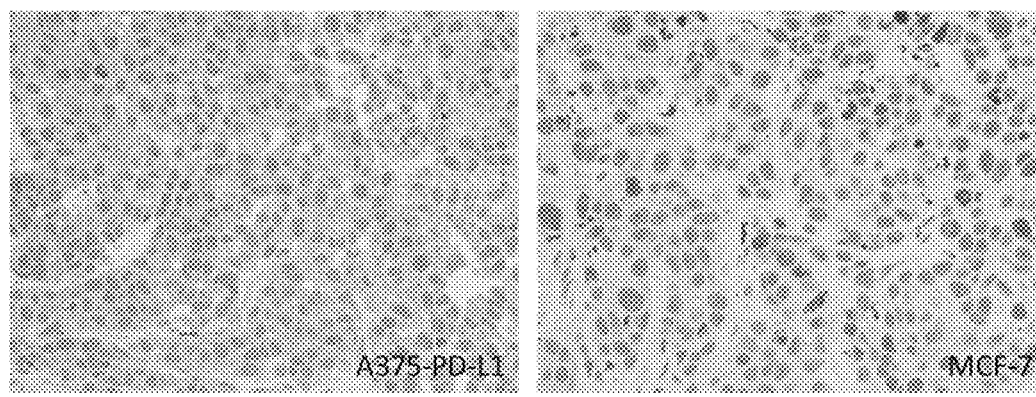

From the results of immunohistochemistry in FIG. 3C, it can be seen that, the A375-PDL1 tumor is positive for PD-L1 expression using 109-chis as the primary antibody and PD-L1 is mainly expressed on the cell surface, and MCF-7 tumors is negative for PD-L1 expression on the cell surface, which is consistent with the results of the flow cytometry.

Example 4: Labeling Single Domain Antibody with Nuclide

Figure 4A:
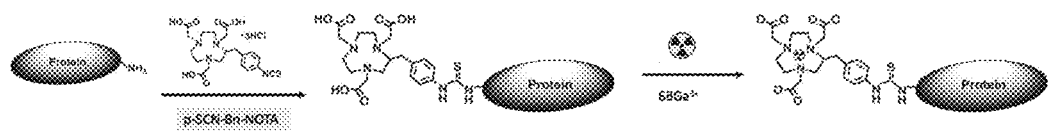

The single domain antibody of the invention was labeled with the chelating agent, p-SCN-Bn-NOTA and the radio-nuclide $^{68}Ga$ according to the flow chart shown in FIG. 4A.

4.1 Reaction of Single Domain Antibody with p-SCN-Bn-NOTA

The single domain antibody, 109-chis (3 mg) was dissolved in 0.05 M of the sodium carbonate buffer at pH 8.7, and the 10-fold molar ratio of excess p-SCN-Bn-NOTA (Macrocyclics, Art. No. B-605) was added. The mixture was stirred at room temperature for at least 18 hours in the dark, and the conjugated product was purified using a PD-10 column (GE) to remove the excess p-SCN-Bn-NOTA, and the single domain antibody was concentrated to ~1 mg/mL by an ultrafiltration tube. SEC-HPL analysis was performed with 0.1 M of the phosphate buffer at pH 7.0 as the mobile phase.

The amount of chelated NOTA was determined by Thermo Scientific LTQ Orbitrap XL liquid chromatography-mass spectrometer. The concentration of the single domain antibody was determined by the kit for determination of concentration of BCA protein. The chromatographic conditions are as follows: Waters ACQUITY UPLC instrument, using the ACQUITY UPLC® BEH C18 1.7 μm (2.1×100 mm) chromatographic column, the autosampler temperature set to 4° C., a flow rate of 0.25 mL/min the column temperature of 50° C., 4 μl of samples, a gradient elution at column temperature, and the mobile phase of 0.1% of the aqueous solution of formic acid (A)-0.1% formic acid-acetonitrile (B). Molecular weight characteristics were calculated using Thermo Scientific Protein Deconvolution 4.0. The obtained mass spectrometry results of single domain antibody 109-chis-NOTA are shown in FIG. 4B.

Figure 4B:
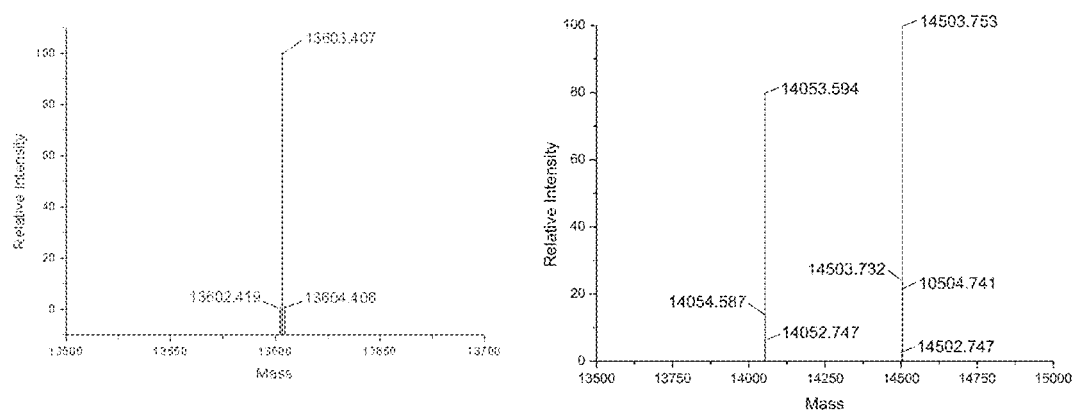

As can be seen from the mass spectrometry results, the molecular weight of the 109-chis protein is 13603 Da as shown in the left panel of FIG. 4B, and after conjugated with NOTA, for 09-chis conjugated with one molecule of NOTA, the corresponding molecular weight was increased by 450 Da, which was 14053 Da, and for 09-chis conjugated with two molecules of NOTA, the corresponding molecular weight was increased by 900 Da, which was 14503 Da, as shown in the right panel of FIG. 4B. The mass spectrometry results of 109-chis-NOTA showed that after the conjugation reaction of 109-chis, the product was a mixture of 109-chis conjugated with one and two molecules of NOTA.

Figure 4C:
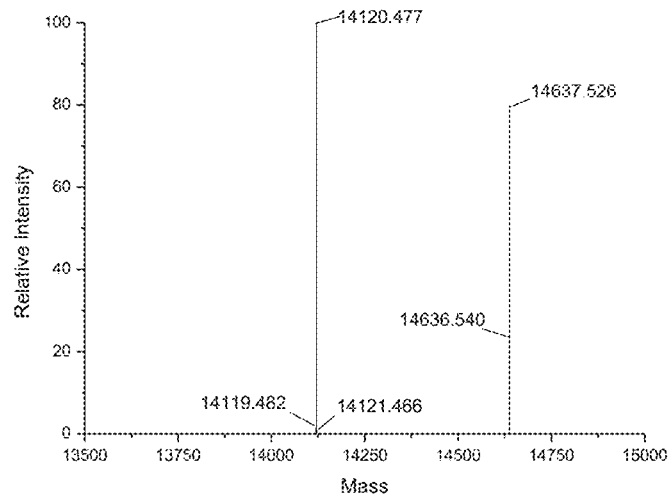

4.2 Synthesis of $^{69, 71}Ga$-NOTA-109-Chis $GaCl_3$ was dissolved in 0.05M of HCL, and ½ volume of 0.2 M of the sodium acetate solution was added, and ¼ volume of 0.1 M of the sodium acetate buffer comprising 109-chis-NOTA at pH 5.3 was added. The pH of the reaction system was between 4.5 and 4.7 and the reaction was performed at room temperature for 10 minutes. The unreacted gallium ion is removed by PD-10 column. The amount of chelated $^{67}Ga$ was determined using Thermo Scientific LTQ Orbitrap XL liquid chromatography-mass spectrometer. The concentration of the single domain antibody was determined by the kit for determination of concentration of BCA protein. The chromatographic conditions are as follows: Waters ACQUITY UPLC instrument, using the ACQUITY UPLC® BEH C18 1.7 μm (2.1×100 mm) chromatographic column, the autosampler temperature set to 4° C., a flow rate of 0.25 mL/min the column temperature of 50° C., 4 μl of samples, a gradient elution, and the mobile phase of 0.1% of the aqueous solution of formic acid (A)-0.1% formic acid-acetonitrile (B). The obtained mass spectrometry results of $^{69,71}Ga$-NOTA-109-chis were shown in FIG. 4C.

The mass spectrometry results of $^{69,71}Ga$-NOTA-109-chis showed that the products were a mixture of proteins chelated with one and two molecules $^{69,71}Ga$.

The molecular weight of 14120 is for one single domain antibody labeled with one molecule of NOTA and one molecule of $^{69,71}Ga$, and the molecular weight of 14637 is for one single domain antibody labeled with two molecules of NOTA and two molecules of [69, 71]Ga. The results demonstrated that under this condition, the corresponding products were successfully obtained by the NOTA conjugation reaction and Ga cold labeling.

4.3 Identification of Binding Ability of [69, 71]Ga-NOTA-109-Chis to PD-L1

The PDL1-Fc fusion protein was transiently expressed by HEK293 and purified by nickel column affinity chromatography. The plate was coated with the obtained PDL1-Fc fusion protein in 0.5 μg/well overnight at 4° C., and then the serial diluted 109-chis PD-L1 single domain antibody proteins or chelated products of PD-L1 single domain antibody protein obtained in 4.2 was added and incubated at room temperature for 1 hour. After washing, the anti-his horseradish peroxidase labeled antibody was added and incubated at room temperature for 1 hour. After washing, the developing solution was added, and the absorption value was read at wavelength of 405 nm. Application software SotfMaxPro v5.4 is used for data processing and mapping analysis. Through four-parameter fitting, the binding curve and the EC50 value of the antibody to PD-L1 were obtained as shown in FIG. 4D to reflect the affinity ability of the 109-chis antibody or its labeled form for PD-L1.

Figure 4D:
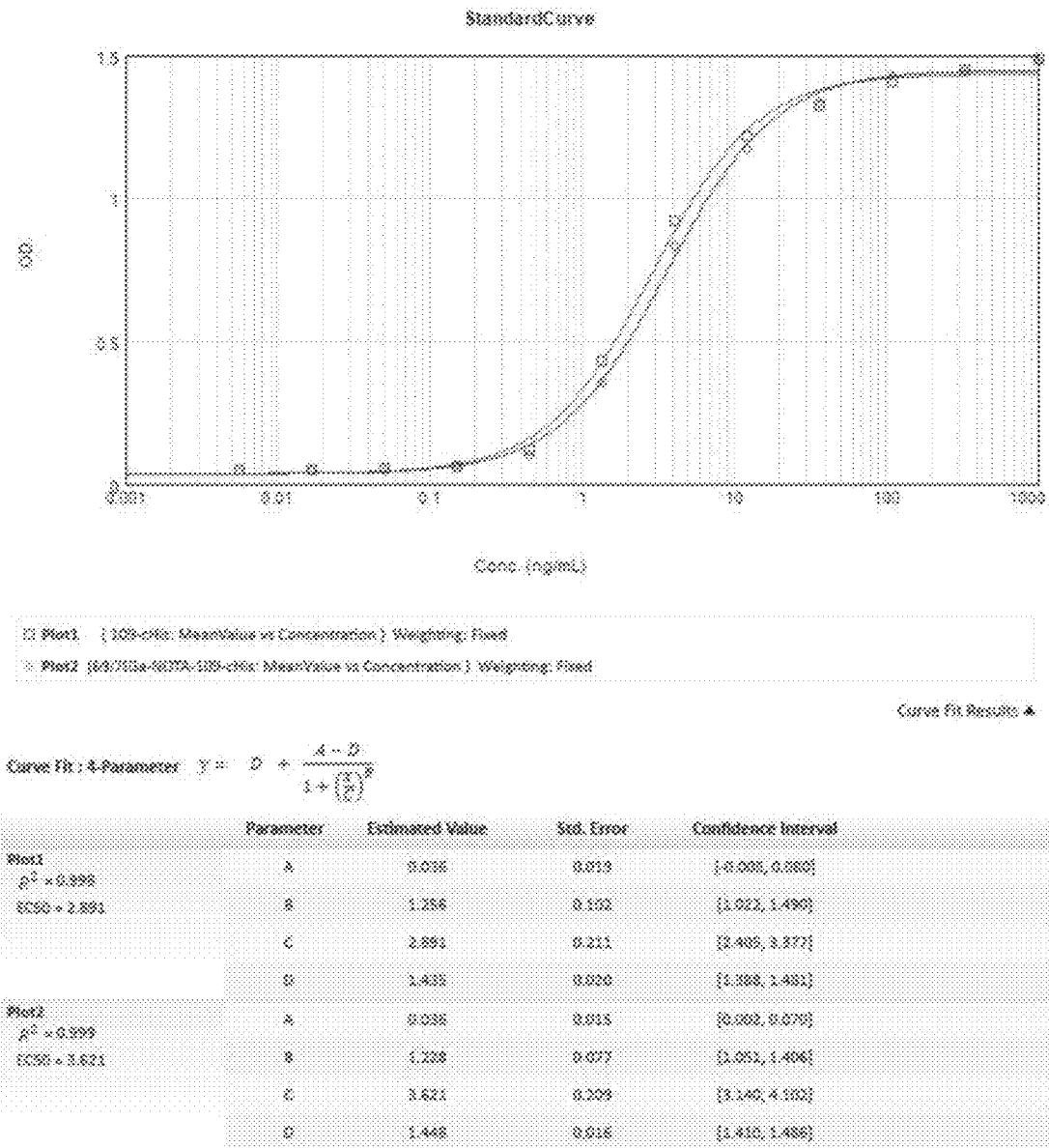

The results are shown in FIG. 4D, wherein the ordinates were OD405 and the abscissas were concentrations of the PD-L1 single domain antibody protein (in ng/mL); the squares represent 109-chis, and the diamonds represent [69,71]Ga-NOTA-109-chis. The two molecules have comparable affinity for PD-L1.

4.4 Synthesis of $^{68}$Ga-NOTA-109-Chis 0.05 M of sterile HCL was used to rinse Eckert & Ziegler GalliaPharm germanium 68/gallium 68 (Ge 68/Ga 68) generator to prepare the $^{68}$Ga eluent, ½ volume of 0.2 M of the sodium acetate solution was added, and ¼ volume of 0.1 M of the sodium acetate buffer containing 109-chis-NOTA at pH of 5.3 was added. The pH of the reaction system is between 4.5 and 4.7, and the reaction was performed at room temperature for 10 minutes. The PD-10 column was used to remove the unreacted gallium ion and the product buffer was replaced with the saline at the same time. The total radioactivity concentration of $^{68}$Ga-NOTA-109-chis injection was analyzed by a dose corrector.

Example 5: Structural Mutation of 109 Antibody

The 109 antibody protein comprises a total of 3 lysine groups with free amino groups on the structure, which can be used for subsequent labeling. In order to optimize the purity of the antibody-labeled chelate and ensure that each mol of the antibody can and can only be conjugated with 1 mol of the chelate, the lysine(s) on the surface of the antibody was mutated, and in order to maintain the affinity, the amino acids adjacent to the lysine were also mutated to obtain a total of 4 kinds of mutants as shown below: 109-R73N&K75E-cHis, 109-K86R&P87A-cHis, 109-RDNSE-cHis, 109-K64Q-cHis, as shown in Table 3. Whether the binding capacity of the mutated antibody to PD-L1 will be affected was also investigated.

TABLE 3

Sequences of 109-chis mutants

| Mutant names | SEQ ID NO | Sequences |
|---|---|---|
| 109-K8 6R&P8 7A-cHis | 8 | METDTLLLWVLLLWVPGSTGQVQLQESGGGSVQAGGS LRLSCTASGFSLDDSDMGWYRQARGNVCQLVSTIASD RSTYYTPSVKGRFTISHDRA<u>KN</u>TIYLQMNSL<u>RA</u>EDTA VYYCAAAPRLAYTTAMTCEGDFAYWGQGTQVTVSSGS MDPGGSHHHHHHHH |
| 109-RD NSE-cH is | 9 | METDTLLLWVLLLWVPGSTGQVQLQESGGGSVQAGGS LRLSCTASGFSLDDSDMGWYRQARGNVCQLVSTIASD RSTYYTPSVKGRFTIS*RDNSE*NTIYLQMNSLKPEDTA VYYCAAAPRLAYTTAMTCEGDFAYWGQGTQVTVSSGS MDPGGSHHHHHHHH |
| 109-K6 4Q-cHis | 10 | METDTLLLWVLLLWVPGSTGQVQLQESGGGSVQAGGS LRLSCTASGFSLDDSDMGWYRQARGNVCQLVSTIASD RSTYYTPS<u>VQ</u>GRFTISHDRA<u>KN</u>TIYLQMNSLKPEDTA VYYCAAAPRLAYTTAMTCEGDFAYWGQGTQVTVSSGS MDPGGSHHHHHHHH |
| 109-R7 3N&K7 5E-cHis | 11 | METDTLLLWVLLLWVPGSTGQVQLQESGGGSVQAGGS LRLSCTASGFSLDDSDMGWYRQARGNVCQLVSTIASD RSTYYTPS<u>VK</u>GRFTISHD<u>NA</u>ENTIYLQMNSLKPEDTA VYYCAAAPRLAYTTAMTCEGDFAYWGQGTQVTVSSGS MDPGGSHHHHHHHH |

5.1 Identification of the Binding Ability of Mutated Antibodies to PD-L1 (ELISA Method)

PDL1-Fc fusion protein was transiently expressed by HEK293 and purified by nickel column affinity chromatography. The plate was coated with the obtained PDL1-Fc fusion protein in 0.5 μg/well overnight at 4° C. The serial diluted obtained PD-L1 single domain antibody protein was then added and incubated at room temperature for 1 hour. After washing, anti-his horseradish peroxidase labeled antibody was added and incubated at room temperature for 1 hour. After washing, the developing solution was added, and the absorption value was read at wavelength of 405 nm. The software SotfMaxPro v5.4 is used for data processing and mapping analysis. Though the four-parameter fitting, the binding curve and the EC50 value of the antibody to PD-L1 were obtained to reflect the affinity of the antibody to PD-L1.

Figure 5A:
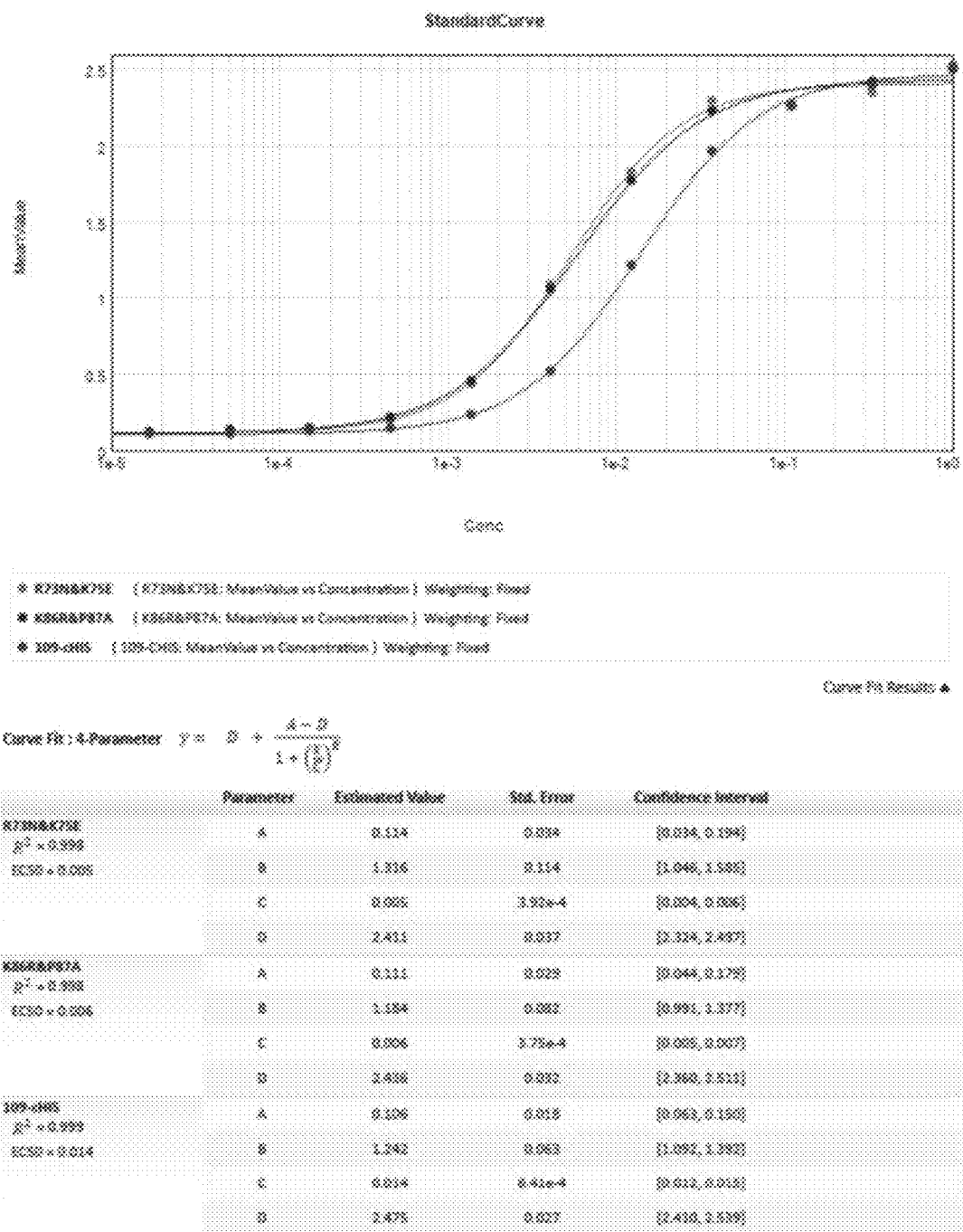
Figure 5B:
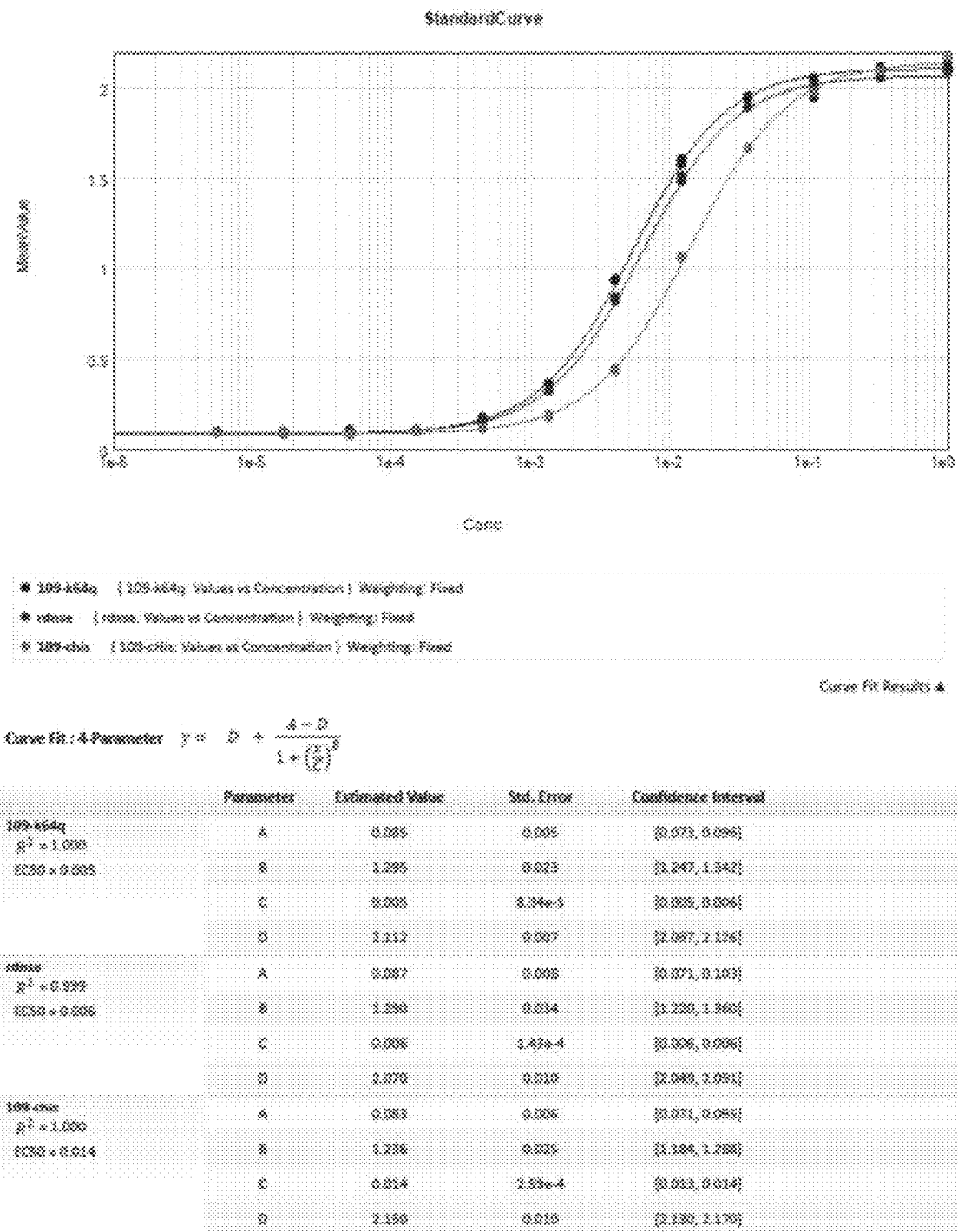

The results were shown in FIGS. 5A-B, wherein the ordinates were OD405, and the abscissas were concentrations of the PD-L1 single domain antibody protein (in ng/mL). EC50 of the mutant with a single lysine mutation slightly decreased compared to that of wild-type 109-chis, indicating that the affinity of the mutant was not destroyed.

5.2 Analysis of NOTA Labeling of Mutated Antibodies

As mentioned above, the amino acid mutation on the surface of antibody did not affect the binding capacity of antigen to antibody. The labeling efficiency of the chelating agent was further analyzed, and the mutated antibody was conjugated with NOTA and identified by the mass spectrometry using the method described in 4.1.

Figure 5C:
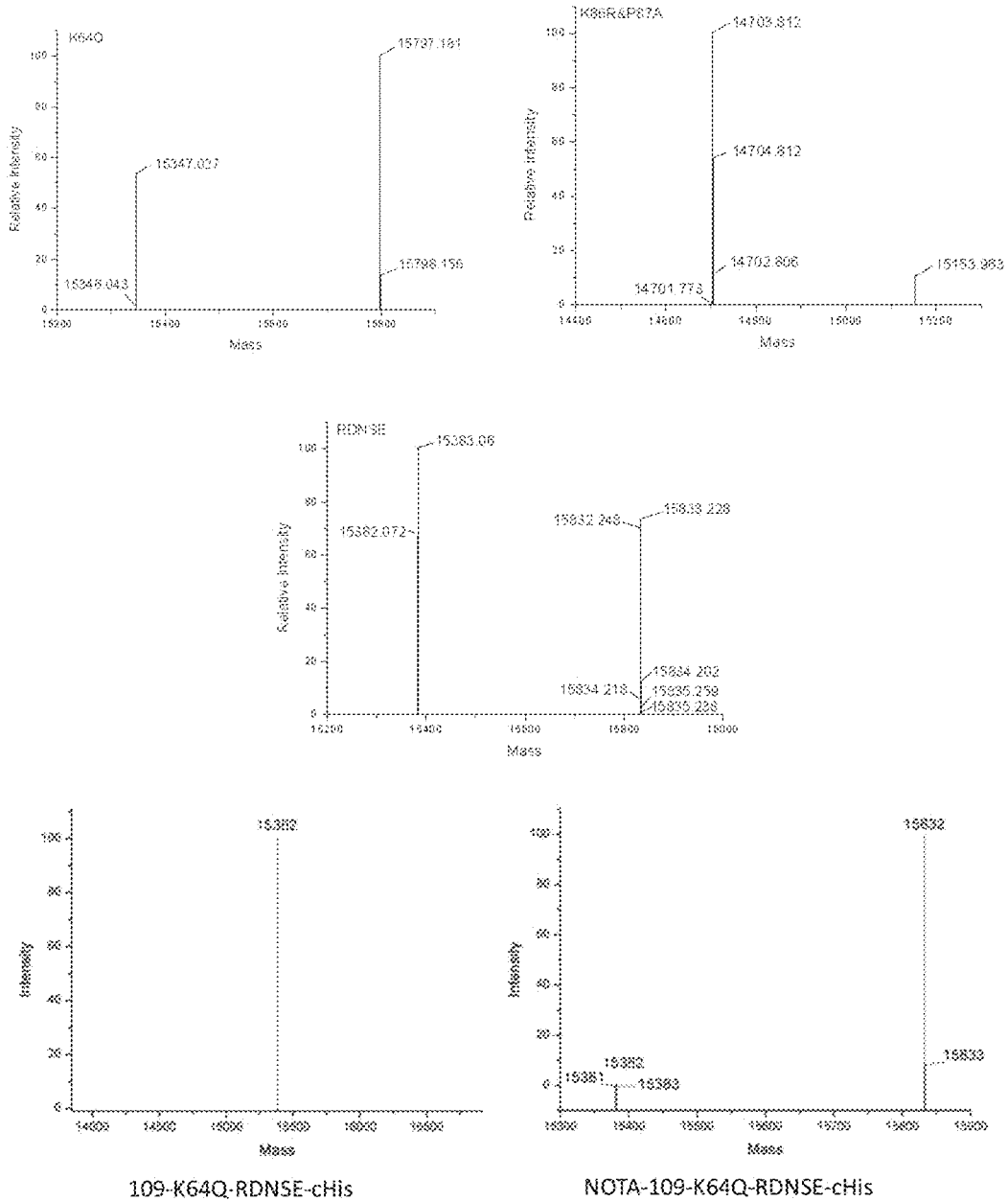

It can be seen from the mass spectrometry results in FIG. 5C that for the K75E and K64Q mutated antibodies, the NOTA conjugation efficiency was not changed due to the amino acid mutation, and after the K86R mutation, NOTA was basically unable to be successfully conjugated to the antibody. This result indicated that K86 was an amino acid that was easily conjugated with NOTA. Therefore, 109-K64Q-RDNSE-cHis was prepared by the K64Q mutation based on the RDNSE mutant protein. 109-K64Q-RDNSE-cHis (SEQ ID NO: 12)
METDTLLLWVLLLWVPGSTGQVQLQESGGGSVQAGGSLRLSCTASGFSL

DDSDMGWYRQARGNVCQLVSTIASDRSTYYTPSVQGRFTISRDNSENTI

YLQMNSLKPEDTAVYYCAAAPRLAYTTAMTCEGDFAYWGQGTQVTVSSG

SMDPGGSHHHHHHHH

Using the method described in 4.1, the mutated antibody, 109-K64Q-RDNSE-cHis was conjugated with NOTA and identified by the mass spectrometry. The mass spectrometry results demonstrated that the product from the reaction of the mutated single domain antibody, 109-K64Q-RDNSE-cHis with the chelating agent, p-SCN-Bn-NOTA was a pure final product conjugated with only one molecule of NOTA.

Example 6: In Vitro Analysis of Single Domain Antibody $^{68}$Ga-NOTA-109 Labeled with Positron Nuclide 6.1 Thin-Layer Chromatography (ITLC) Analysis ITLC SA are pre-cut to 1 cm×12 cm strips and the ends of the strips were marked with a pencil at a distance of 1 cm from each other. The solution of ammonium acetate 1M:methanol (1:1 V/V) was dumped into the developing tank to a depth of 3 to 4 mm and the tank was covered and be equilibrated. A drop of $^{68}$Ga-109 injection was dropped at the pencil line 1 cm from the bottom of the ITLC strip. The ITLC strip was placed in the developing tank and the sample was developed 10 cm from the loading point (i.e., to the top pencil line mark). The ITLC scanning was performed with a radiometric ITLC scanner, and the radiochemistry Purity (RCP) was calculated by integrating the peaks on the chromatogram. The analysis results were shown in FIG. 6A, indicating that the single domain antibody 109 was successfully labeled with the positron nuclide $^{68}$Ga.

6.2 SEC-HPLC and In Vitro Stability Analysis

SEC-HPLC chromatographic conditions are as follows: SEC-HPLC was performed on Agilent 1100 series HPLC equipped with the Tokou sv3000SL (4.6×250 mm) column and Raytest GABI radioactivity detector. SEC analysis was performed with 0.1 M phosphate buffer at pH 7.0 as the mobile phase.

A representative SEC-HPLC chromatogram of the radiolabeled single domain antibody purified on a PD-10 column was shown in FIG. 6A. In the UV chromatogram at 280 nm, the retention time of the radiolabeled single domain antibody was practically unchanged compared to that of the corresponding unlabeled single domain antibody (except for the time difference in the physical separation of UV and γ detectors; the data was not shown).

The radiolabeled antibody was stored in normal saline for 3 hours at room temperature. The SEC results demonstrated that there was no obvious degradation or $^{68}$Ga dissociation (FIG. 6B), indicating that the radiolabeled antibody was basically stable under this condition.

Figure 9:
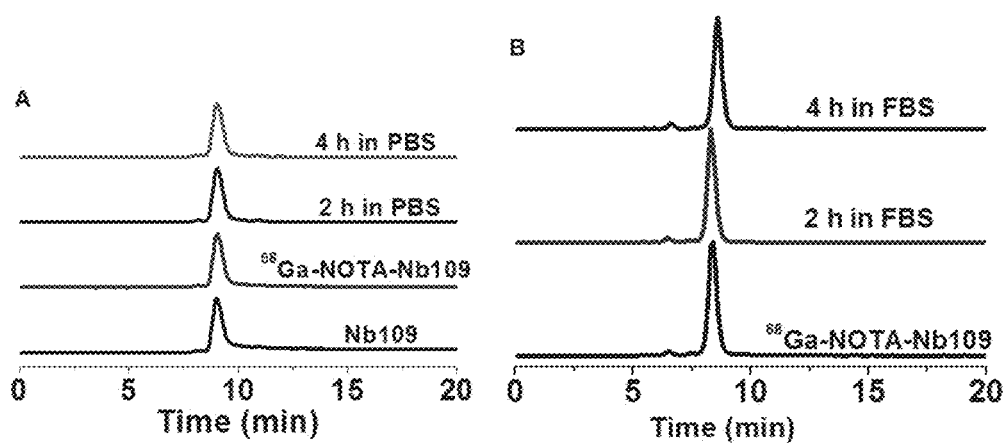
FIG. 9 illustrates in vitro stability of $^{68}$Ga-NOTA-109 in PBS and serum (FBS), respectively.

The labeled radiolabeled product, 68Ga-NOTA-109 was placed in PBS and the serum (FBS) and stored at room temperature for 0, 2, and 4 hours, and analyzed by HPLC to observe its stability in PBS and FBS. The results are shown in FIGS. 9A and 9B. The results demonstrated that after the prepared radiolabeled product was placed in PBS and the serum at room temperature for 4 hours, there was no difference in the peak shape compared to that of the radiolabeled products before storage. The radiochemistry purity was >98%, and no significant dissociation was observed.

Figure 10:
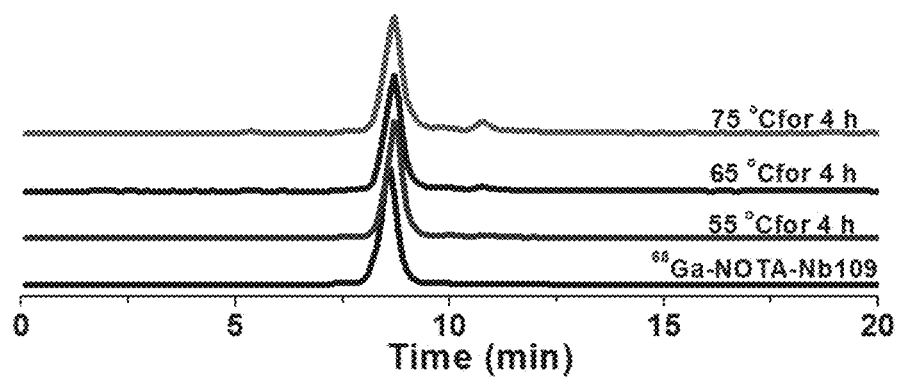
FIG. 10 illustrates in vitro stability of $^{68}$Ga-NOTA-109 in PBS at various temperatures.

Subsequently, the labeled radiolabeled product, 68Ga-NOTA-109 was placed in PBS and stored at 55-75° C. for 4 hours (FIG. 10) to determine its temperature stability in vitro. The results demonstrated that after the prepared radiolabeled product was placed in PBS at 55° C. for 4 hours, there was no difference in the peak shape compared to that of the radiolabeled products before storage. The radiochemistry purity was >98% and no significant dissociation was observed. When the radiolabeled product was placed in PBS at 65° C. and 75° C. for 4 hours, there was a degradation peak behind the main peak, and the amount of degradation increases with the temperature rising.

6.3 Cell Binding and Endocytosis Analysis

Cells were plated in 6-well plates with 8×10$^5$ cells per well and 3 mL of medium/well and cultured at 37° C. and 5% $CO_2$ overnight. The cells were taken out and incubated at 4° C. for 30 min. All of the 6-well plates were taken out and the medium in the plates was replaced with the medium containing 10 μci (~50 nM) heat-labeled protein, and the plates were incubated for 1 h at 4° C.; and the medium in the 3 wells of the plates was replaced with the medium containing 25 μM of the unlabeled protein as control samples for non-specific adsorption. The medium containing the unbound protein in the supernatant was sucked out. The cells were washed with 2 mL of pre-cooled PBS containing 1% BSA twice and were supplemented with the growth medium and incubated at 37° C. and 5% $CO_2$ for 1 h and 2 h. After the cells were incubated for different periods, the supernatants from two tests were taken out, and the cells were supplemented with 2 mL of PBS containing 20 mM of sodium acetate at pH 3.0, and incubated at 4° C. for 15 min, and supplemented with 2 mL of PBS containing 20 mM of sodium acetate at pH 3.0 again. These two supernatants were mixed, which were for the cpm value of the parts bound to the cell surface. The remaining cell pellets were resuspended in PBS containing 0.5% SDS, which were for the cpm value of the parts involving to endocytosis. The cpm values of the parts involving to cell binding and endocytosis were measured by the gamma counter and subjected to attenuation correction. The results were shown in FIG. 6C, indicating that $^{68}$Ga was not basically dissociated after the endocytosis and the radiolabeled antibody was stable in structure.

6.4 Stability Analysis In Vivo

Healthy mice were selected, and each was injected with 0.1 mL of $^{68}$Ga-NOTA-109 with the radiochemistry purity of 98% through the tail vein. The urine was taken 2 hours after the injection and analyzed by HPLC to determine the stability of $^{68}$Ga-NOTA-109 in vivo.

Figure 11:
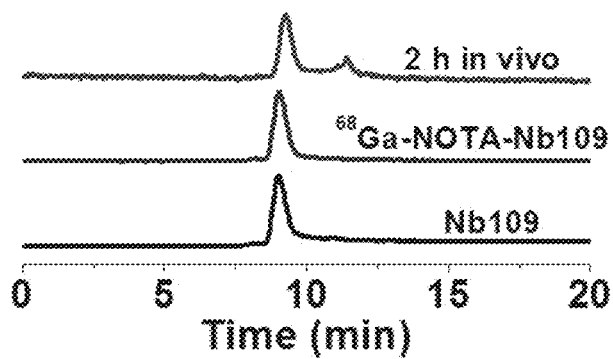
FIG. 11 illustrates in vivo stability of $^{68}$Ga-NOTA-109.

The results were shown in FIG. 11, 2 hours after the radiopharmaceutical injected into the mice, the main peak shape of the radionuclide in the urine was not different from that of the radiolabeled product while there was a degradation peak behind the main peak.

Example 7: $^{68}$Ga-NOTA-109 Immunological Activity Assay

The immunological activity of $^{68}$Ga-NOTA-109 was determined as follows.

(1) cells are digested and plated, incubated overnight at 37° C. and 5% $CO_2$, and then incubated at 4° C. for 30 min.

(2) the digested cells were resuspend in 500 μL of PBS (pH 7.4) to the cell density of 3×10$^6$ cells/tube, and 1000-fold excess of the unlabeled 109 single domain antibody or blocking antibody KN035 (a therapeutic antibody that can block the binding of PD1 to PDL1) was added 0.5 h earlier respectively.

(3) the cells were added with 1 (5 μci/0.2 μg) of the radioactive reaction solution and incubated at room temperature for 0.5, 1, 2, and 4 hours.

(4) The cells in the flow tube were centrifuged at 600 g for 2 minutes to transfer the supernatant into a new flow sorting tube. The cells were washed twice with pre-cooled 500 μL of PBS, and all of the supernatants from the washing were added to the flow tube that was previously centrifuged and the cells were resuspended in 500 μL PBS.

(5) the cpm value of cell suspensions and supernatants from washing were determined by the γ counter, and subjected to attenuation correction.

Figure 12:
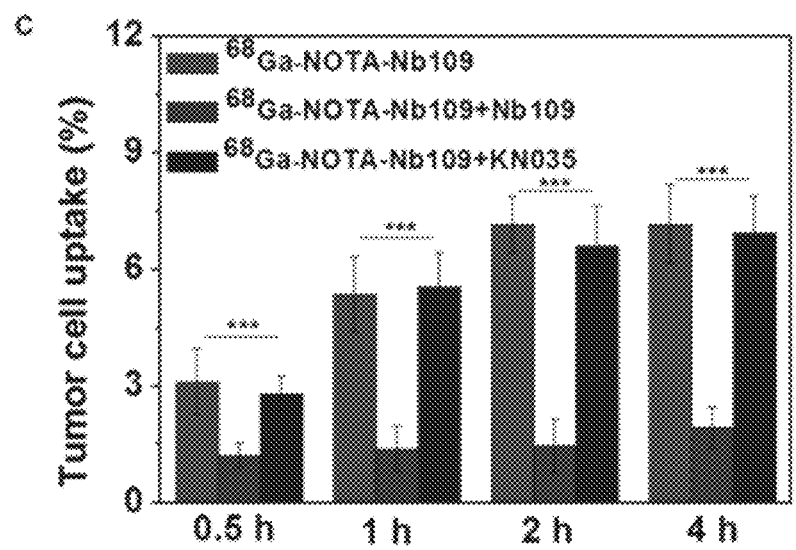
FIG. 12 illustrates immunological activity detection of $^{68}$Ga-NOTA-109.

The results were shown in FIG. 12. The cell uptake of $^{68}$Ga-NOTA-109 can reach 7.17% 4 hours after the reaction, and the cell uptake of the cells pretreated with a blocking drug KN035 in advance can reach 6.93%, which were basically the same. The experimental groups pretreated with excess non-labeled single domain antibody 109 showed that the cell uptake of $^{68}$Ga-NOTA-109 can be significantly impeded, and the cell uptake within 0.5-4 h was basically between 1 and 2%.

Example 8: In Vivo Distribution of 68Ga-NOTA-109

8.1 Animal Model Used for Studying $^{68}$Ga-NOTA-109.

Female nude mice aged 6-8 weeks were used for in vivo studies. The nude mice were raised in an SPF environment, with free access to food and water, in standard 12-hour day-night lighting cycle. For heterotransplantation, 100 μl of cells (A375-PDL1 or MCF-7)/PBS were implanted subcutaneously in the right front leg of the mice. The cell inoculation density is about 5-6×10$^6$ cells/mouse. The implantation was performed under isoflurane anesthesia. Under these conditions, in more than 80% of the injected animals, usable tumors (100-300 mm$^3$) (A375-PDL1 or MCF-7) were obtained after 3 to 4 weeks.

8.2 In Vivo Distribution of $^{68}$Ga-NOTA-109

~10 μg of radiolabeled single domain antibody (~100 μCi/10 μg) was injected into mice via the tail vein. The mice were placed in a cage lined with filter papers until euthanized. At each time point, five mice were euthanized, the tissues of interest were dissected, and counted by the gamma counter. The data were collected form blood, kidney, liver, spleen, lung, heart, intestine, stomach, muscle, skin, brain, bone and tumor. The injection dose was taken as the total injection dose. For each of the organs, the % of injection dose was determined based on the total injection dose, and the organ was weighed to determine the % of injection dose per gram (% ID/g).

Figure 7A:
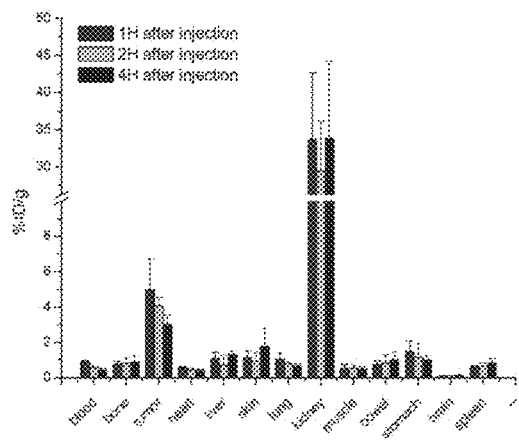

Table 4 shows the biodistribution data of $^{68}$Ga-NOTA-109 uptake in intact male mice bearing A375-PD-L1 tumors, which was the biodistribution data in vitro of $^{68}$Ga-NOTA-109 uptake in the intact male mice with subcutaneous tumors (n=5). Data were collected 1, 2, 4 h after intravenous administration. The data are expressed as average % ID/g±standard deviation (S.D.). The error of the ratio was calculated as the geometric mean of the standard deviation. The data were shown in FIG. 7A, in which the error bars represent the standard deviation of the group, and the results demonstrated good specificity of 68Ga-NOTA-109 to tumors.

TABLE 4

| | In vivo distribution data of 68Ga-NOTA-109 | | | | | |
|---|---|---|---|---|---|---|
| | 1 h | | 2 h | | 4 h | |
| | X | SD | X | SD | X | SD |
| Blood | 0.912124 | 0.077211 | 0.57594 | 0.086296 | 0.44498 | 0.092117 |
| Bone | 0.7887 | 0.146195 | 0.84844 | 0.287182 | 0.88583 | 0.348184 |
| Tumor | 5.003894 | 1.721763 | 4.08413 | 0.436109 | 3.036376 | 0.517282 |
| Heart | 0.58276 | 0.050193 | 0.468654 | 0.076802 | 0.417402 | 0.065193 |
| Liver | 1.111892 | 0.334403 | 2.64046 | 3.163882 | 1.31615 | 0.172084 |
| Skin | 1.152078 | 0.38249 | 0.946656 | 0.492711 | 1.781012 | 1.004551 |
| Lung | 1.053976 | 0.360583 | 0.80478 | 0.07103 | 0.682806 | 0.098499 |
| Kidney | 33.66316 | 8.969117 | 29.44267 | 6.698076 | 33.84909 | 10.39923 |
| Muscle | 0.536532 | 0.232919 | 0.545652 | 0.166952 | 0.520984 | 0.089335 |
| Intestine | 0.742312 | 0.234935 | 0.834458 | 0.458166 | 2.226896 | 2.73239 |
| Stomach | 1.48044 | 0.598261 | 1.162074 | 0.742917 | 1.01634 | 0.229507 |
| Brain | 0.107954 | 0.023349 | 0.127018 | 0.009794 | 0.127242 | 0.019301 |
| Spleen | 0.635144 | 0.058496 | 0.667098 | 0.175658 | 0.840284 | 0.244376 |

Figure 7B:
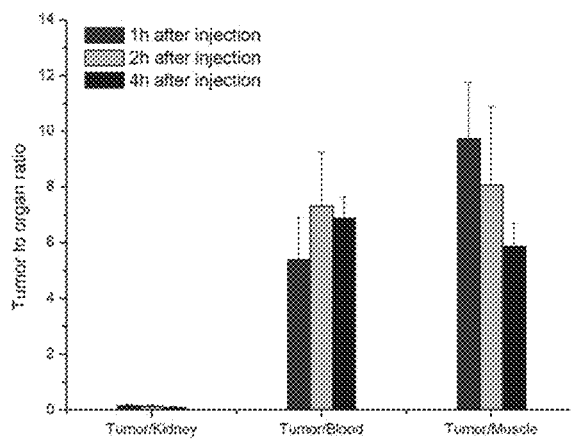

The results of the uptake ratio of tumor tissue to blood and the uptake ratio of tumor tissue to contralateral normal muscle from these experiments were shown in FIG. 7B. The 109 single domain antibody showed good tumor uptake in A375-PDL1 tumors expressing the target, and the maximum value was about 5% of the injected dose per gram of tissue, 30 minutes after injection (PI). The peak ratio of tumor to muscle was still greater than 6, 4 h after PI. Compared with that of the contralateral normal muscle, the uptake of tumor tissues in the mice exhibited high uptake. The uptake of bone was low after 4 hours, indicating that the marker was stable in vivo without dissociation of $^{68}$Ga and may become a good tumor contrast agent.

8.3 In Vivo PET Imaging with $^{68}$Ga-NOTA-109

The mice were anesthetized with isoflurane and placed on a PET bed, and ~10 μg of the radiolabeled single domain antibody (~100 μCi/10 μg) was injected into the tail vein. Continuous PET scans were performed at 120 minutes to analyze the radioactive uptake of tumor, muscle and kidney at a plurality of time points, as shown in the upper and middle panels of FIG. 7C. The two-dimensional ordered subset expectation maximization algorithm is used for image reconstruction. The radioactivity (MBq/mL) was calculated by the region of interest (ROI) method in organs such as tumors, muscles, and liver. The obtained value was divided by the injected dose to obtain the uptake value of PET tracer (% ID/g) in each tissue (assuming that the tissue density was 1 g/ml). The calculated results were shown in FIG. 7D.

In the blocking experiment, a therapeutic drug KN035 (which can block the binding of PD1 to PDL1) was administered 24 hours in advance. After the distribution of the therapeutic drug was completed, the mice were anesthetized with isoflurane and placed on the PET bed. ~10 μg of the radiolabeled single domain antibody (~100 μCi/10 μg) was injected into the tail vein of the mice. Continuous PET scans were performed at 120 minutes to analyze the radioactive uptake of tumor, muscle, and kidney at a plurality of time points, as shown in the bottom panel of FIG. 7C. The biodistribution was analyzed using the activity time curve of MIM software, as shown in FIG. 7D.

Figure 7C:
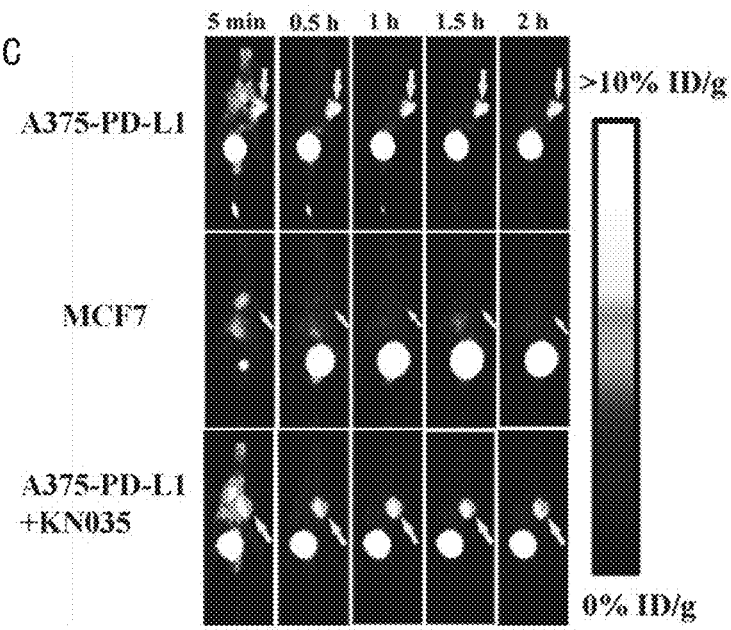
Figure 7D:
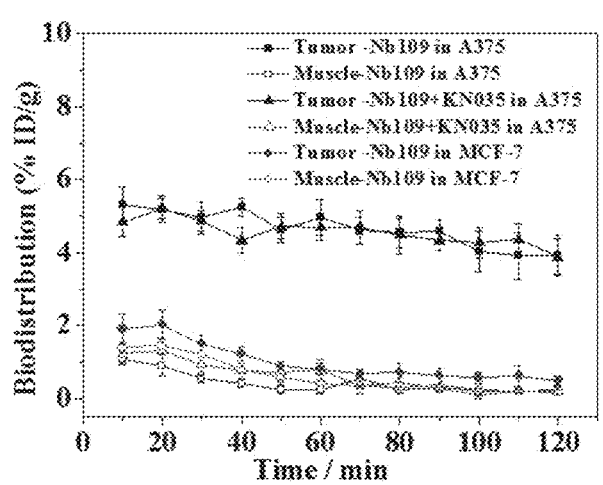

As shown in FIGS. 7C and 7D, the A375-PD-L1 transplanted tumors were clearly visible from 5 to 120 minutes after the injection of the PET tracer $^{68}$Ga-NOTA-109. 120 minutes after the MCF-7 transplanted tumors with negative PD-L1 expression were injected, no uptake was observed. It can be seen from FIG. 7C that the A375-PD-L1 tumor had good contrast compared to the contralateral side.

$^{68}$Ga-NOTA-109 was significantly concentrated in the kidney of the model mice, indicating that it was mainly metabolized by the kidney. $^{68}$Ga-NOTA-109 had a short half-life and did not cause damage to the model mice.

10 min after the injection, the uptake value of $^{68}$Ga-NOTA-109 in the tumor reached a maximum of about 5-6% ID/g. With the change of time, the uptake value was not obviously decreased. 120 min after the injection, the uptake value of $^{68}$Ga-NOTA-109 in the tumor can still be maintained at about ~4% ID/g. The uptake value of $^{68}$Ga-NOTA-109 in the kidney was significant, confirming that the PET tracer is mainly metabolized by the kidney. In addition, as shown in FIG. 7D, the uptake of $^{68}$Ga-NOTA-109 in the tumor was more significantly than that in the normal tissues such as muscle, and the uptake ratio of tumor-to-muscle (T/NT) is greater than 5 which was a benefit to obtain high-definition PET images for tumors for diagnosis and treatment of tumors.

8.4 In Vivo PET Imaging of $^{68}$Ga-NOTA-109 in a Same Mouse to Analyze PD-L1 Targeting Ability In order to further prove the PD-L1 targeting ability of $^{68}$Ga-NOTA-109 and eliminate individual differences, different cancer cells, A375-HPD-L1, a A375-HPD-L1/A375 mixture (1/1, v/v) and A375 were simultaneously subcutaneously inoculated on the left hind leg, the right hind leg and the right front leg of the same mouse, respectively. At the beginning of the experiment, the size of the tumor was about 250-350 mm$^3$.

Figure 13:
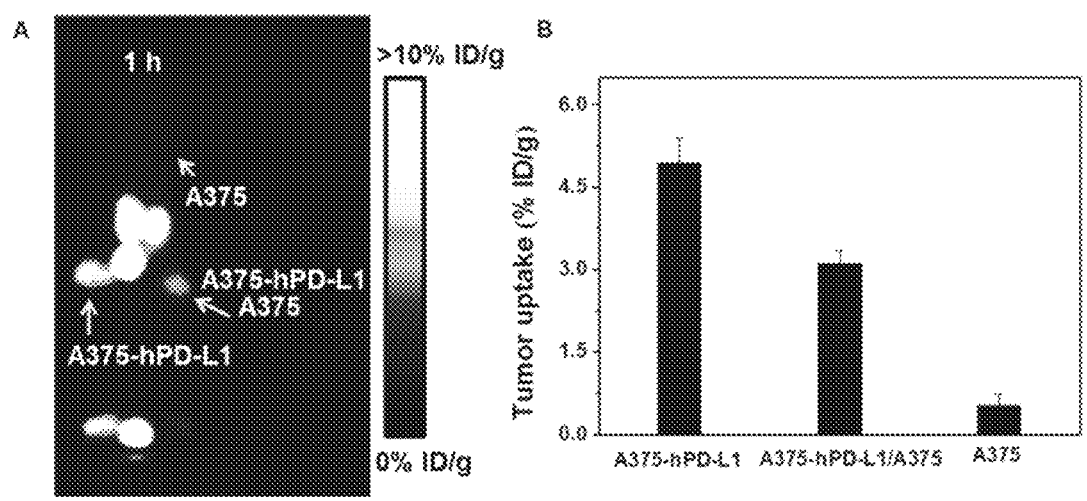
FIG. 13 illustrates PET imaging of $^{68}$Ga-NOTA-109 in different transplanted tumors in the same mouse. A: one hour after injection, a static image of $^{68}$Ga-NOTA-109; B: biodistribution of $^{68}$Ga-NOTA-109 in tumors according to the ROI quantitative analysis of PET images.

~10 μg of the radiolabeled single domain antibody (~100 μCi/10 μg) was injected into the mice via the tail vein. The static PET scanning was performed 1 h after administration, as shown in FIG. 13A.

The two-dimensional ordered subset expectation maximization algorithm is used for image reconstruction. For tumors, the region of interest (ROI) method was used to calculate the radioactivity (MBq/mL). The value was divided by the injection dose to obtain the uptake value of PET tracer (% ID/g) for each tissue (assuming that the tissue density is 1 g/ml). The calculated results were shown in FIG. 13B.

The results demonstrated that 60 minutes after the injection of the above-mentioned PET tracer, $^{68}$Ga-NOTA-109, A375-PD-L1 transplanted tumors were clearly visible, and the radioactive uptake reached 4.94±0.46% id/g. The transplanted tumors inoculated with the A375-HPD-L1/A375 mixture (1/1, v/v) showed a relatively intermediate uptake, while the A375 transplanted tumors with negative expression of PD-L1 showed no uptake 60 minutes after the injection. It can be seen from the calculation of ROI that, in the same animal, the three transplanted tumors had obvious differences in % ID/g due to different expression levels.

Figure 14:
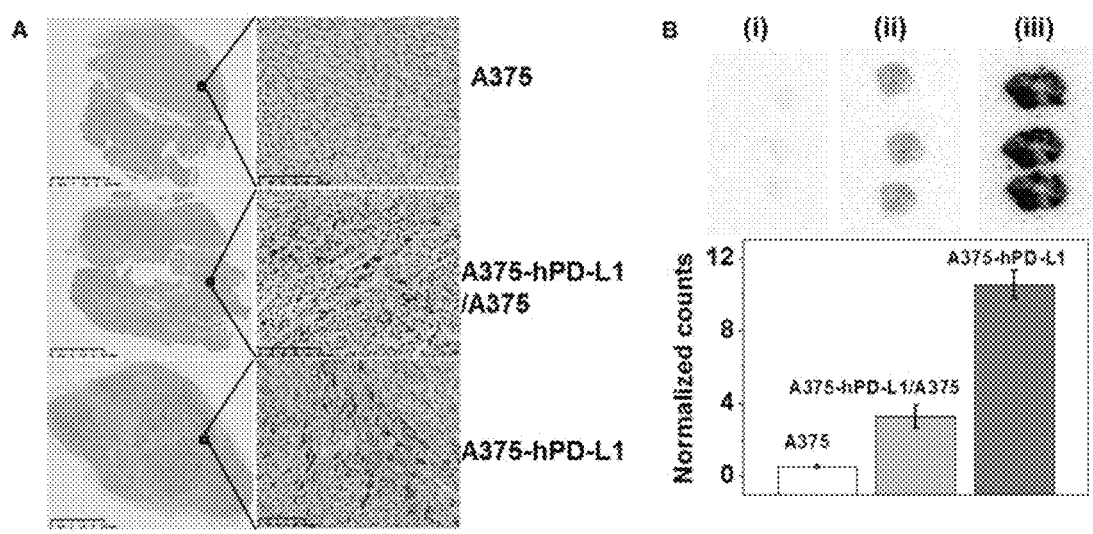
FIG. 14 illustrates autoradiography and immunohistochemical analyses of different transplanted tumors in the same mouse after PET imaging with Ga-NOTA-109. A: PD-L1 immunohistochemical staining of tumors. B: $^{68}$GA-NOTA-109 autoradiography analyses (top) and autoradiography quantitative analyses (bottom) in A375(i), A375/A375-HPD-L1(ii), and A375-HPD-L1(iii) tumors.

After the PET imaging was completed, the tumors were removed from the animal and subjected to autoradiography and immunohistochemical staining analysis (FIG. 14). The expression of PD-L1 detected by immunohistochemistry showed that the PD-L1 positive areas of A375-HPD-L1 and A375-HPD-L1/A375 tumors were 30%±6.36 and 15%±4.24, respectively, while A375 tumors were basically negative. The results of the tumor autoradiography in vitro further confirmed the results of immunohistochemistry.

Example 9: $^{125}$I-Labeled Single Domain Antibody 109 and Imaging 10 mg/mL of the chloramine T solution and the sodium metabisulfite solution were formulated with 0.05 mol/L of PBS at PH=7.5 as the solvent. 2 μl of the protein was diluted into 50 μl of the PB solution. 50 μl of the solution was taken and added to 1.5mCi (10 μl) Na$^{125}$I for mixing. The chloramine T solution was added to the mixed solution and mixed quickly to react at room temperature for 40 s. 50 μl of the sodium metabisulfite solution was added and the reaction was terminated. A drop of reaction liquid was sucked with a capillary dropped on the tail of the chromatography paper, and developed to the top of the chromatography paper with PBS as a developing agent for termination. The labeling rate is identified by a TLC scanner. The unreacted $^{125}$I was removed by the PD-10 column and the product buffer system was replaced with the physiological saline at the same time.

Figure 8:
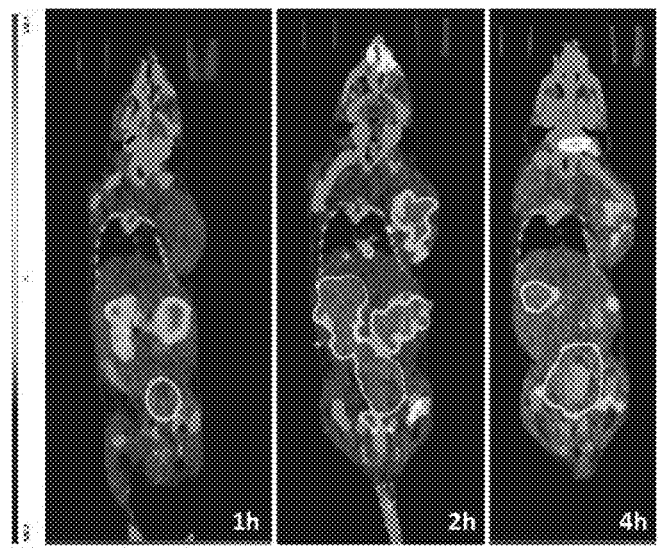
FIG. 8 illustrates SPECT result of $^{125}$I-labeled single domain antibody 109.

The A375-PDL1 tumor model was inoculated according to the method in 8.1, the mice were anesthetized with isoflurane and placed on the SPECT bed, and ~10 μg of the radiolabeled single domain antibody (~100 μCi/10 μg) was injected into the tail vein. The SPECT scanning were performed at 1 h, 2 h, and 4 h to analyze radioactive uptake of tumors, tissues and organs at a plurality of time points, as shown in FIG. 8.

120 minutes after injection of $^{125}$I-109, A375-PD-L1 transplanted tumors were clearly visible. It can be seen from the Figures that the A375-PD-L1 tumor has good contrast compared to the contralateral side. Similar to the performance of $^{68}$Ga-NOTA-109 in the model mice, $^{125}$I-109 was significantly concentrated in the kidney, indicating that it was mainly metabolized by the kidney.

What we claimed is:

1. A programmed death ligand 1 (PD-L1) binding polypeptide which is capable of specifically binding to PD-L1 and comprises at least one immunoglobulin single variable domain, wherein the at least one immunoglobulin single variable domain comprises:
   CDR1, which comprises the amino acid sequence set forth in SEQ ID NO: 5,
   CDR2, which comprises the amino acid sequence set forth in SEQ ID NO: 6 or the amino acid sequence set forth in SEQ ID NO: 13, and
   CDR3, which comprises the amino acid sequence set forth in SEQ ID NO: 7.

2. The PD-L1 binding polypeptide of claim 1, wherein the at least one immunoglobulin single variable domain comprises:
   CDR1, which comprises the amino acid sequence set forth in SEQ ID NO: 5, CDR2,
   which comprises the amino acid sequence set forth in SEQ ID NO: 13, and CDR3,
   which comprises the amino acid sequence set forth in SEQ ID NO:7.

3. The PD-L1 binding polypeptide of claim 1, wherein the immunoglobulin single variable domain comprises an amino acid sequence that is at least 80% identical to the amino acid sequence of SEQ ID NO:1, and comprises:
   CDR1, which comprises the amino acid sequence set forth in SEQ ID NO: 5,
   CDR2, which comprises the amino acid sequence set forth in SEQ ID NO: 6 or the amino acid sequence set forth in SEQ ID NO: 13, and
   CDR3, which comprises the amino acid sequence set forth in SEQ ID NO: 7.

4. The PD-L1 binding polypeptide of claim 1, wherein the immunoglobulin single variable domain comprises an amino acid sequence selected from the group consisting of SEQ ID NO: 1-2, 8-12 and 18-22.

5. The PD-L1 binding polypeptide of claim 1, wherein the immunoglobulin single variable domain is VHH.

6. A nucleic acid molecule encoding the PD-L1 binding polypeptide of claim 1.

7. An expression vector comprising the nucleic acid molecule of claim 6 operably linked to an expression regulatory element.

8. A host cell comprising the nucleic acid molecule of claim 6, and being capable of expressing the PD-L1 binding polypeptide.

9. A method for producing a PD-L1 binding polypeptide, comprising:
   a) culturing the host cell of claim 8 under a condition allowing expression of the PD-L1 binding polypeptide;
   b) recovering the PD-L1 binding polypeptide expressed by the host cell from the culture obtained from step a); and c) optionally further purifying and/or modifying the PD-L1 binding polypeptide obtained from step b).

10. A conjugated molecule which comprises the PD-L1 binding polypeptide of claim 1 and at least one detectable marker conjugated to the PD-L1 binding polypeptide.

11. The conjugated molecule of claim 10, wherein the PD-L1 binding polypeptide is conjugated to the detectable marker via a chelating agent.

12. The conjugated molecule of claim 11, wherein the PD-L1 binding polypeptide comprises the amino acid sequence set forth in SEQ ID NO: 12.

13. A diagnostic agent for detecting and/or diagnosing PD-L1 related diseases, which comprises the PD-L1 binding polypeptide of claim 1, and optionally a physiologically acceptable carrier.

14. A kit comprising the PD-L1 binding polypeptide of claim 1.

* * * * *